United States Patent

Ichihashi

(10) Patent No.: US 12,274,894 B2
(45) Date of Patent: Apr. 15, 2025

(54) RADIOTHERAPY PLANNING APPARATUS, RADIOTHERAPY PLANNING METHOD, AND RADIOTHERAPY SUPPORT APPARATUS

(71) Applicant: Canon Medical Systems Corporation, Otawara (JP)

(72) Inventor: Masahide Ichihashi, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 453 days.

(21) Appl. No.: 17/651,071

(22) Filed: Feb. 15, 2022

(65) Prior Publication Data

US 2022/0257979 A1 Aug. 18, 2022

(30) Foreign Application Priority Data

Feb. 15, 2021 (JP) .................... 2021-021690
Feb. 14, 2022 (JP) .................... 2022-020612

(51) Int. Cl.
*A61N 5/10* (2006.01)

(52) U.S. Cl.
CPC ......... *A61N 5/1039* (2013.01); *A61N 5/1037* (2013.01)

(58) Field of Classification Search
CPC . A61N 5/103; A61N 1/00; A61N 5/00; A61N 5/1031; A61N 5/1038; A61N 5/1039; A61N 2005/1041; A61N 5/1049; A61N 2005/1054; A61N 2005/1056; A61N 2005/1062; A61N 5/1064; A61N 5/1065; A61N 5/1071; A61N 5/1067; A61N 2005/1074; A61B 5/0036
See application file for complete search history.

(56) References Cited

U.S. PATENT DOCUMENTS

2020/0282231 A1   9/2020   Khuntia et al.
2021/0101023 A1*  4/2021   Abel .................... A61N 5/1042

FOREIGN PATENT DOCUMENTS

JP          2010-220659 A      10/2010

OTHER PUBLICATIONS

Combined Chinese Office Action and Search Report issued Jun. 28, 2024 in Chinese Patent Application No. 202210137349.4, 8 pages.

* cited by examiner

*Primary Examiner* — Don K Wong
(74) *Attorney, Agent, or Firm* — Oblon, McClelland, Maier & Neustadt, L.L.P.

(57) ABSTRACT

According to one embodiment, a radiotherapy planning apparatus includes processing circuitry. The processing circuitry set irradiation conditions for a medical image relating to a patient. The processing circuitry acquires a histogram of a radiation dose rate in a predetermined area in the patient based on the irradiation conditions. The processing circuitry evaluates the irradiation conditions based on the histogram. The processing circuitry outputs information based on an evaluation result of the irradiation conditions.

15 Claims, 10 Drawing Sheets

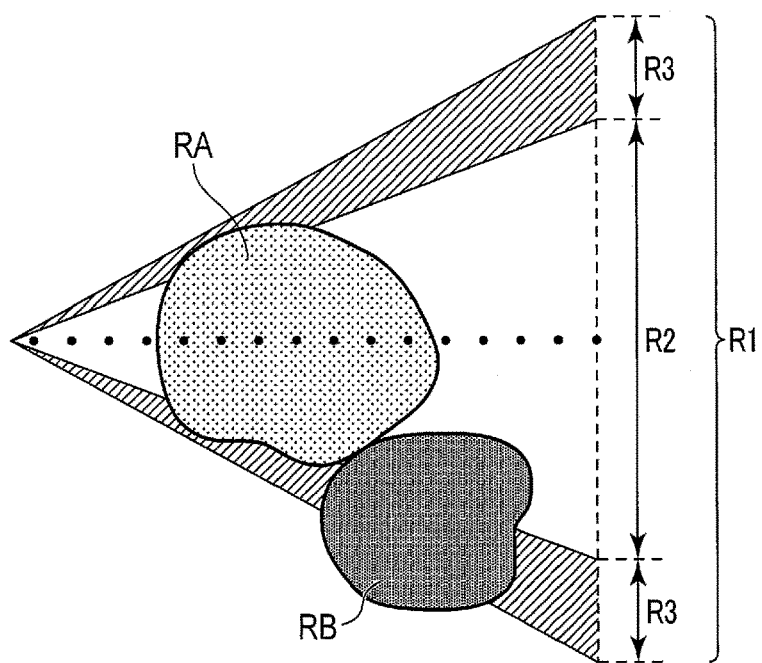
F I G. 4
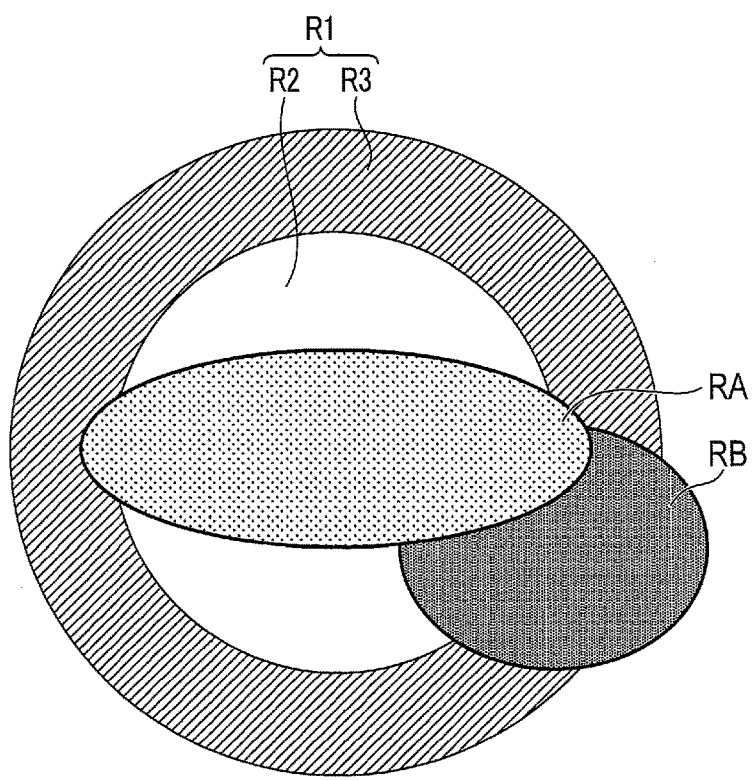
F I G. 5

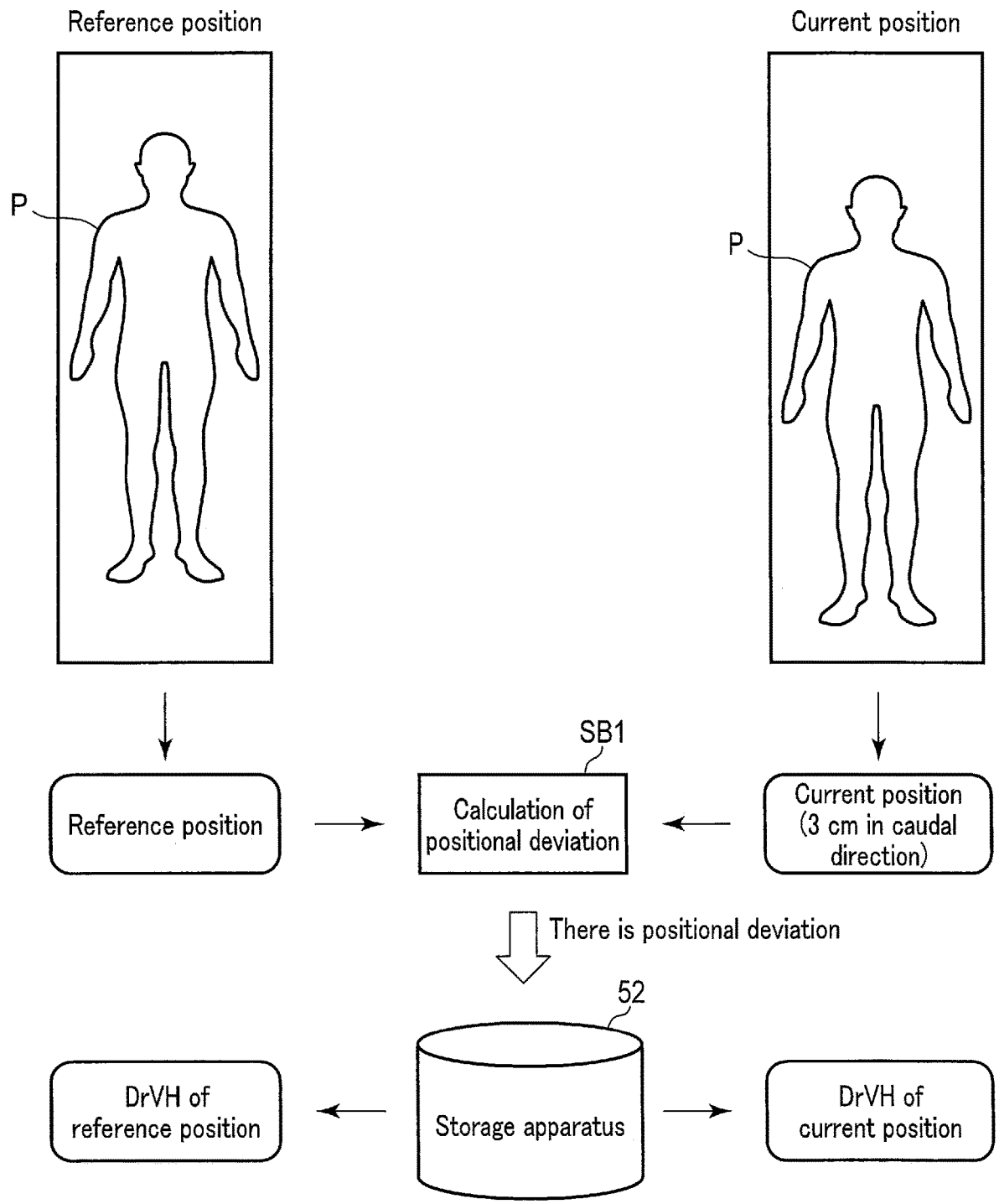
F I G. 13

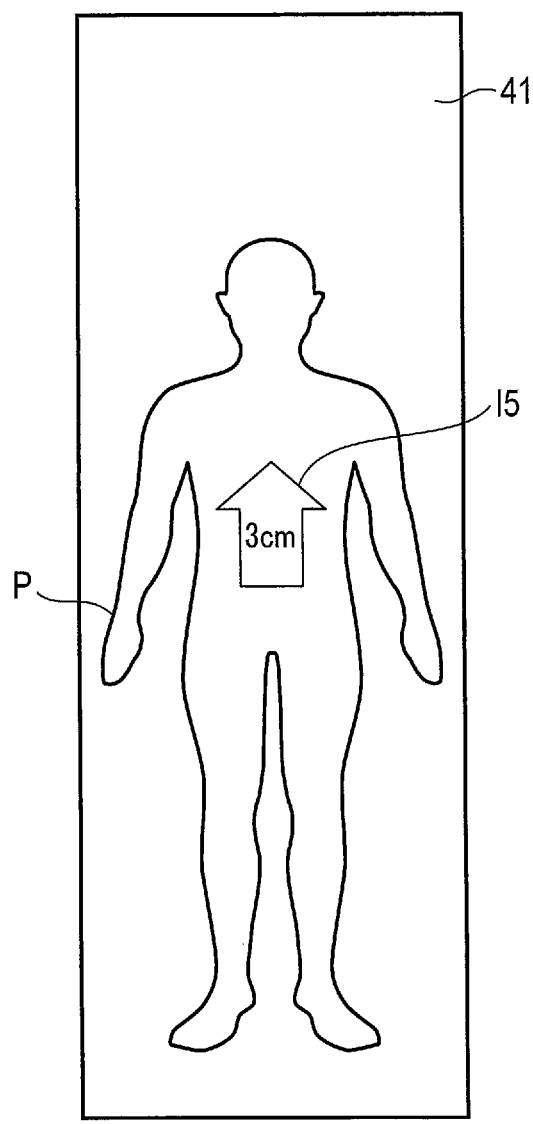
F I G. 16

RADIOTHERAPY PLANNING APPARATUS, RADIOTHERAPY PLANNING METHOD, AND RADIOTHERAPY SUPPORT APPARATUS

CROSS-REFERENCE TO RELATED APPLICATIONS

This application is based upon and claims the benefit of priority from Japanese Patent Application No. 2021-21690, filed Feb. 15, 2021; and No. 2022-20612, filed Feb. 14, 2022; the entire contents of which are incorporated herein by reference.

FIELD

Embodiments described herein relate generally to a radiotherapy planning apparatus, a radiotherapy planning method, and a radiotherapy support apparatus.

BACKGROUND

An ultra-high dose-rate, short radiation method called "FLASH radiotherapy" is known in the field of radiotherapy. FLASH radiotherapy is a technique for selectively damaging a tumor without damaging healthy tissue by radiation at an ultra-high dose-rate (for example, 40 Gy/sec) for a short time (for example, 1 second or shorter). However, a dose rate is reduced in a penumbra, which is caused by a collimator that restricts an irradiation field, and for this reason, it the penumbra is irradiated on healthy tissue, the effects of FLASH radiotherapy cannot be attained and a possibility of damaging healthy tissue arises.

BRIEF DESCRIPTION OF THE DRAWINGS

FIG. 4 is a diagram schematically showing a FLASH area and a normal irradiation field in the cross section parallel to a beam axis of radiation when the irradiation direction is 270 degrees.

FIG. 5 is a diagram schematically showing a FLASH area and a normal irradiation field in the cross section perpendicular to a beam axis of radiation when the irradiation direction is 270 degrees.

FIG. 13 is a diagram schematically showing a series of processes relating to the acquisition of DrVH of a current position and a DrVH of a reference position.

FIG. 16 is a diagram showing a projection example of a direction of correction and an amount of correction.

DETAILED DESCRIPTION

A radiotherapy planning apparatus according to an embodiment includes processing circuitry. The processing circuitry sets irradiation conditions for a medical image relating to a patient. The processing circuitry acquires a histogram of a radiation dose rate in a predetermined area in the patient based on the irradiation conditions. The processing circuitry evaluates the irradiation conditions based on the histogram. The processing circuitry outputs information based on a result of evaluation of the irradiation conditions.

Hereinafter, the embodiments of a radiotherapy planning apparatus and a radiotherapy support apparatus will be explained in detail with reference to the accompanying drawings.

The radiotherapy planning apparatus and radiotherapy support apparatus according to the present embodiment is included in a radiotherapy system.

Figure 1:
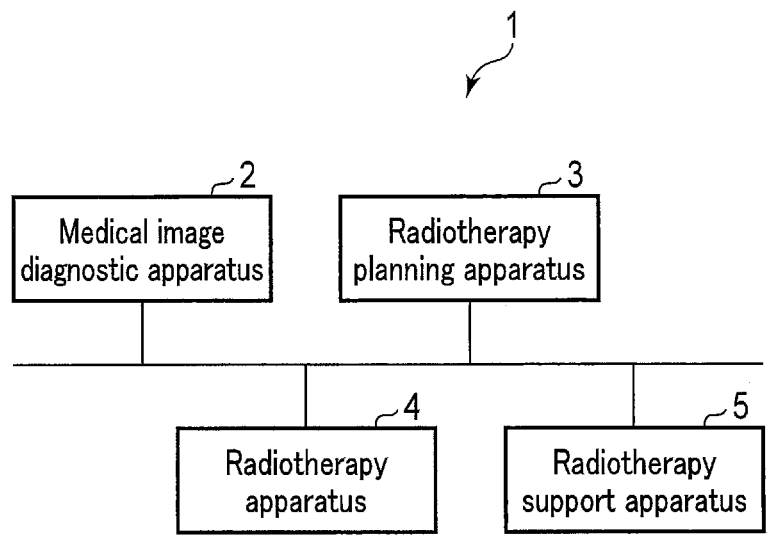
FIG. 1 is a diagram showing a configuration example of a radiotherapy system according to a first embodiment.

FIG. 1 is a diagram showing a configuration example of a radiotherapy system 1 according to the present embodiment. As shown in FIG. 1, the radiotherapy system 1 has a medical image diagnostic apparatus 2, a radiotherapy planning apparatus 3, a radiotherapy apparatus 4, and a radiotherapy support apparatus 5. The medical image diagnostic apparatus 2, the radiotherapy planning apparatus 3, the radiotherapy apparatus 4, and the radiotherapy support apparatus 5 are connected to each other via a network in such a manner that they can communicate with each other. The radiotherapy system 1 is a system with which a therapeutic plan relating to radiotherapy for a patient is produced and radiotherapy is performed in accordance with the therapy plan.

The medical image diagnostic apparatus 2 performs medical imaging on a patient who is a target for therapy, to produce a medical image used for therapy planning. A medical image may be a two-dimensional image including a plurality of two-dimensionally arranged pixels, or a three-dimensional image including a plurality of three-dimensionally arranged voxels. The medical image diagnostic apparatus 2 may be any type of modality capable of generating a medical image. Examples of a modality apparatus are an X-ray computed tomography apparatus, a magnetic resonance imaging apparatus, a cone beam CT apparatus, and a nuclear medicine diagnostic apparatus. Data of a medical image is transmitted to the radiotherapy planning apparatus 3, for example.

The radiotherapy planning apparatus 3 is a computer configured to produce a therapeutic plan for a patient using medical images produced by the medical image diagnostic apparatus 2. Data of the therapeutic plan is supplied to the radiotherapy apparatus 4 and the radiotherapy support apparatus 5.

The radiotherapy apparatus 4 performs a therapy on a patient in accordance with the therapeutic plan produced by the radiotherapy planning apparatus 3. The radiotherapy apparatus 4 has a treatment gantry and a treatment bed provided in a treatment room. The treatment bed moves the top plate in such a manner that a treatment targeted body part of the patient approximately matches an isocenter. The treatment gantry supports an irradiation head rotatably around a rotation axis. The irradiation head emits radiation in accordance with the therapeutic plan.

Specifically, the irradiation head forms an irradiation field with a multi-divided collimator (multi-leaf collimator) to reduce irradiation on healthy tissue. By irradiating the body part targeted for treatment with radiation, the lesion is annihilated or reduced.

The radiotherapy support apparatus 5 is situated in a treatment room where the radiotherapy apparatus 4 is installed or in a control room next to the treatment room. The radiotherapy support apparatus 5 is a computer configured to output guide information for guiding work relating to radiotherapy.

Hereinafter, an embodiment of the radiotherapy planning apparatus 3 is described as a first embodiment and an embodiment of the radiotherapy support apparatus 5 is described as a second embodiment.

First Embodiment

Figure 2:
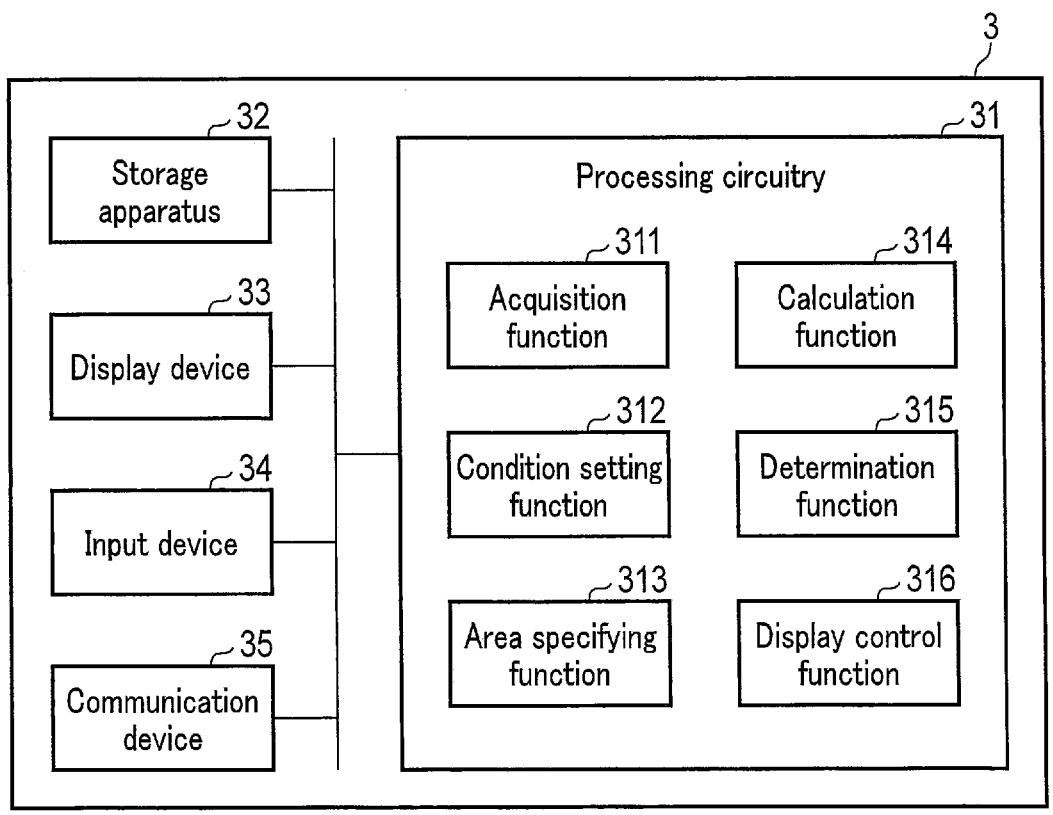
FIG. 2 is a diagram showing a configuration example of a therapy planning apparatus according to the first embodiment.

FIG. 2 is a diagram showing a configuration example of the radiotherapy planning apparatus 3 according to the first embodiment. The radiotherapy planning apparatus 3 includes processing circuitry 31, a storage apparatus 32, a display device 33, an input device 34, and a communication device 35.

The processing circuitry 31 includes processors such as a CPU (central processing unit) and a GPU (graphics processing unit). When the processor activates a radiotherapy planning program installed onto the storage apparatus 32, etc., the processor realizes the acquisition function 311, the condition setting function 312, the area specifying function 313, the calculation function 314, the determination function 315, and the display control function 316. Note that the embodiment is not limited to the case in which the respective functions 311 to 316 are realized by a single processing circuit. Processing circuitry may be composed by combining a plurality of independent processors, and the respective processors may execute programs, thereby realizing the functions 311 to 316.

By the realization of the acquisition function 311, the processing circuitry 31 acquires various information items. For example, the processing circuitry 31 acquires medical image data received from the medical image diagnostic apparatus 2.

By the realization of the condition setting function 312, the processing circuitry 31 sets irradiation conditions relating to radiotherapy. The irradiation conditions at least include an irradiation field and an application dose index value. An irradiation field is an area on which radiation is irradiated. An application dose index value is a dose index value of radiation to be applied. A dose index value includes a total dose indicating a total amount of an irradiated dose and a dose rate indicating a dose irradiated per unit of time.

By the realization of the calculation function 314, the processing circuitry 31 calculates, based on the irradiation conditions that are set by the condition setting function 312, a volume index value of an area in normal tissue included in an irradiation field and relating to a predicted dose index value that falls below a first threshold. The predicted dose index value is a dose index value calculated by the processing circuitry 31, etc. at the time of planning radiotherapy, and is a predicted value of a dose index value of irradiation on a location corresponding to each pixel of a medical image. Specifically, the predicted dose index value includes a predicted dose value which is a predicted value of a total dose and a predicted dose value which is a predicted value of a dose rate. The volume index value is an index value relating to a volume and includes, for example, a volume and a volume ratio, etc.

By the realization of the determination function 315, the processing circuitry 31 determines whether or not the irradiation condition set by the condition setting function 312 is accepted based on the volume index value calculated by the calculation function 314. For details, the processing circuitry 31 determines that the irradiation conditions are not accepted if the volume index value exceeds a second threshold, and determines that the conditions are accepted if the volume index value falls below the second threshold.

The processing circuitry 31 causes the display device 33 to display various types of information by the realization of the display control function 316. For example, the processing circuitry 31 displays the volume index value calculated by the calculation function 314 and a determination result obtained by the determination function 315, and the like.

The storage apparatus 32 is a type of storage device for storing various types of information, such as a ROM (read only memory), a RAM (random access memory), an HDD (Hard Disk Drive), an SSD (Solid State Drive), or a semiconductor memory device, etc. The storage apparatus 32 is not limited to the above-listed memory apparatuses but may be a driver that writes and reads various types of information in and from, for example, a portable storage medium such as a compact disc (CD), a digital versatile disc (DVD), a flash memory, or a semiconductor memory. The storage apparatus 32 may be provided in an external computer connected to the radiotherapy planning apparatus 3 via a network. For example, the storage apparatus 32 stores a therapy planning program, etc.

The display device 33 displays various types of information through the display control function 316 of the processing circuitry 31. For the display device 33, for example, a liquid crystal display (LCD), a cathode ray tube (CRT) display, an organic electro luminescence display (OELD), a plasma display, or any other display can be used as appropriate. The display device 33 may be a projector. The input device 34 accepts various kinds of input operations from a user, converts the accepted input operations to electric signals, and outputs the electric signals to the processing circuitry 31. Specifically, as the input device 34, a mouse, a keyboard, a trackball, a switch, a button, a joystick, a touchpad, a touch panel display, etc. can be used as appropriate. The input device 34 outputs electrical signals to the processing circuitry 31 according to an input operation. The input device 34 may be a speech recognition device that converts audio signal collected by a microphone into command signals. The input device 34 may be an input device provided in an external computer connected to the system via a network, etc.

The communication device 35 is an interface for data communication with other apparatuses included in the radiotherapy system 1. For example, the communication device 35 receives medical image data from the medical image diagnostic apparatus 2 via a network. The communication device 35 transmits data of the therapy plan to the radiotherapy apparatus 4 or the radiotherapy support apparatus 5 via a network.

Next, an operation example of the radiotherapy planning apparatus 3 is explained. Suppose a medical image in the following explanations is a three-dimensional CT image collected by an X-ray computed tomography apparatus.

Figure 3:
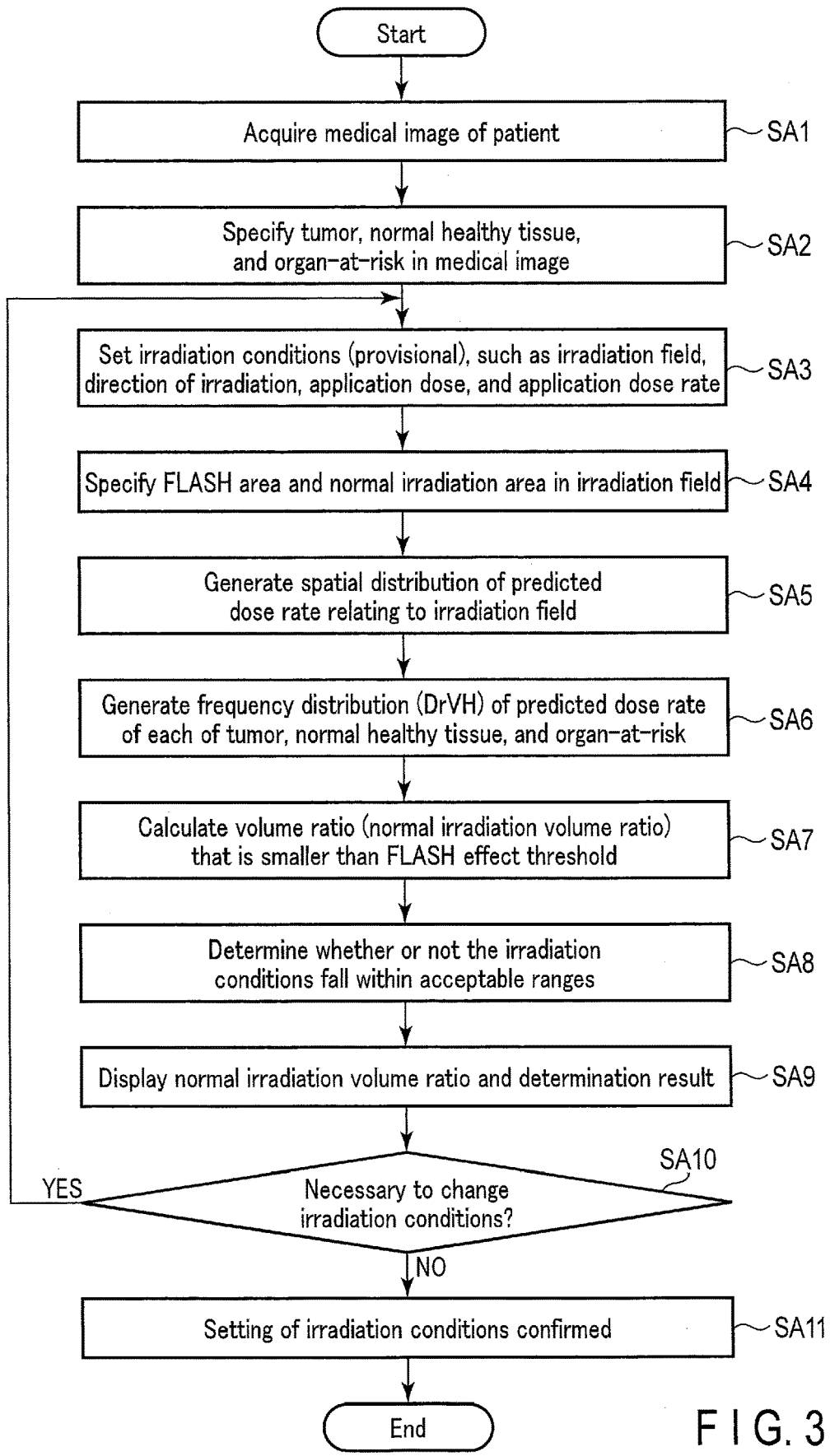
FIG. 3 is a diagram showing a typical flow of a therapy planning process by the radiotherapy planning apparatus.

FIG. 3 is a diagram showing a typical flow of a therapy planning process by the radiotherapy planning apparatus 3. As shown in FIG. 3, the processing circuitry 31 first acquires a medical image of a patient through the realization of the acquisition function 311 (step SA1). In a medical image acquired in step SA1, anatomical structures of the patient are drawn.

After step SA1 is performed, the processing circuitry 31 specifies, through the realization of the area specifying function 313, a tumor, normal healthy tissue, and an organ-at-risk in the medical image acquired in step SA1 (step SA2). A tumor is a target of radiotherapy. Normal healthy tissue and an organ-at-risk are healthy tissue other than a tumor. An organ-at-risk is an organ having a high radiation sensitivity and included in healthy tissue. Normal healthy tissue is healthy tissue other than an organ-at-risk. It suffices that these areas are specified with a discretionarily chosen method. For example, the areas may be specified manually by a user. The specifying process is performed with the following procedures. First, the processing circuitry 31 causes the display device 33 to display a medical image. The user draws outlines with the input device 34 such as a mouse or a tablet pen, etc. around each of a tumor, normal healthy tissue and an organ-at-risk that are drawn out in the medical image. The processing circuitry 31 specifies the image areas surrounded by the outlines as a tumor, normal healthy tissue, or an organ-at-risk. If there are multiple tumor areas, normal healthy tissue areas, and organs-at-risk, they are individually specified.

The specifying method is not limited to the above-described method and this specifying process may be automatically performed by image processing. For example, the processing circuitry 31 is able to specify a tumor, normal healthy tissue, and an organ-at-risk by performing threshold processing or image recognition processing on a medical image.

After step SA2, the processing circuitry 31, through the realization of the condition setting function 312, sets provisional irradiation conditions (step SA3). In step SA3, the processing circuitry 31 sets an irradiation field, a irradiation direction, and an application dose index value as irradiation conditions. The irradiation field is set within the medical image. The irradiation direction is a direction of irradiation. The irradiation direction is defined by an angle with respect to the rotation center axis of the treatment gantry of the radiotherapy apparatus 4. The application dose index value includes an application dose and an exposure rate. The application dose is defined as a total dose of irradiation during radiotherapy conducted over a few days. The application dose is defined by an irradiation dose per unit of time.

After step SA3 is performed, the processing circuitry 31 specifies, through the realization of the area specifying function 313, a FLASH area and a normal irradiation area in the irradiation field set in step SA3 (step SA4). In step SA4, the processing circuitry 31 specifies the irradiation area which is irradiated with the penumbra radiation from the irradiation field set in step SA3 as a normal irradiation area, and specifies the irradiation area which is irradiated with the non-penumbra radiation as a FLASH area.

FIGS. 4 and 5 are drawings schematically showing a FLASH area and a normal irradiation area when the irradiation direction is 270 degrees. FIG. 4 shows a cross section of a medical image parallel to a beam axis of radiation. FIG. 5 shows a cross section of a medical image orthogonal to a beam axis of radiation. As shown in FIGS. 4 and 5, the medical image includes a tumor area RA and a healthy tissue area RB. The tumor area RA is an image area relating to the tissue specified in step SA3. The healthy tissue area RB is an image area relating to the normal healthy tissue and/or the organ-at-risk specified in step SA3.

As shown in FIGS. 4 and 5, the irradiation field R1 is set in such a manner that it surrounds the tumor area RA. The area reduced by a predetermined distance from the irradiation field R1 is set as a FLASH area R2. The area between the irradiation field R1 and the FLASH area R2 is set as a normal irradiation area R3. The normal irradiation area R3 is an area irradiated with a radiation beam through the collimator provided in the radiotherapy apparatus 4, namely a penumbra irradiation area. It suffices that a predetermined distance is set in accordance with geometric conditions, etc. of the radiotherapy apparatus 4. A predetermined distance on the order of 5 mm is assumed in the present embodiment. The FLASH area R2 is an area irradiated with a direct beam that does not pass the collimator provided in the radiotherapy apparatus 4, namely a radiation beam not relating to a penumbra, and a FLASH irradiation is realized.

As described above, the FLASH irradiation is an irradiation method for selectively damaging a tumor without damaging healthy tissue with irradiation at a high dose for a short time. An effect of selectively damaging a tumor without damaging healthy tissue will be called a "FLASH irradiation effect" hereinafter. Since the dose rate in the normal irradiation area R3 is lower than that of the FLASH irradiation, there is no FLASH irradiation effect on the normal irradiation area R3; on the other hand, since an irradiation at a high dose rate compared to a dose rate of normal radiotherapy is applied, there is a possibility of damaging healthy tissue to a greater extent. For this reason, a smaller volume of the healthy tissue area RB to be superposed on the normal irradiation area R3 is more preferable as an irradiation condition.

After step SA4, the processing circuitry 31 generates, through the realization of the calculation function 314, a spatial distribution of a predicted dose rate relating to the irradiation field specified in step SA3 (step SA5). In step SA5, the processing circuitry 31 generates a spatial distribution of a predicted dose rate in accordance with a discretionarily selected dose calculation algorithm based on the irradiation conditions and the medical image. The predicted dose rate is calculated as a predicted value of an administered dose rate relating to a single time of FLASH irradiation. At this time, the processing circuitry 31 allocates the predicted dose rate reduced by the collimator to the normal irradiation area and allocates the predicted dose rate not reduced by the collimator to the FLASH area so as to generate a spatial distribution of the predicted dose rates. As a dose calculation algorithm, an equivalent TAR (tissue-air ratio) method, a differential scattering air dose ratio method, a micro volume method, a Monte Carlo method, and a convolution method, etc. are available, for example.

After step SA5, the processing circuitry 31 generates, through the realization of the calculation function 314, a frequency distribution of a predicted dose rate (DrVH) of each of the tumor, the normal healthy tissue, and the organ-at-risk specified in step SA2 (step SA6). For example, the processing circuitry 31 specifies a predicted dose rate allocated to each of the pixels in the normal tissue area corresponding to each of the normal healthy tissue and the organ-at-risk, and calculates a volume index value of the predicted dose rate. The processing circuitry 31 is capable of generating a DrVH by recording the volume index value of each predicted dose rate. As a volume index value, either a volume or a volume ratio may be used. A volume may be defined by the number of pixels or by a value obtained by multiplying the number of pixels with a volume of a single pixel. A volume ratio is defined as a ratio of a volume of each predicted dose rate to a total volume of a healthy tissue area. Hereinafter, suppose that the volume index value is a volume ratio. The processing circuitry 31 is capable of generating DrVH similarly to each tumor area.

After step SA6, the processing circuitry 31 calculates the volume ratio that is lower than the FLASH effect threshold through the realization of the calculation function 314 (step SA7). The calculated volume ratio is called a "normal irradiation volume ratio". Specifically, in step SA7, the processing circuitry 31 calculates a normal irradiation volume ratio by applying the FLASH effect threshold to the DrVH of the normal tissue area generated in step SA6.

Figure 6:
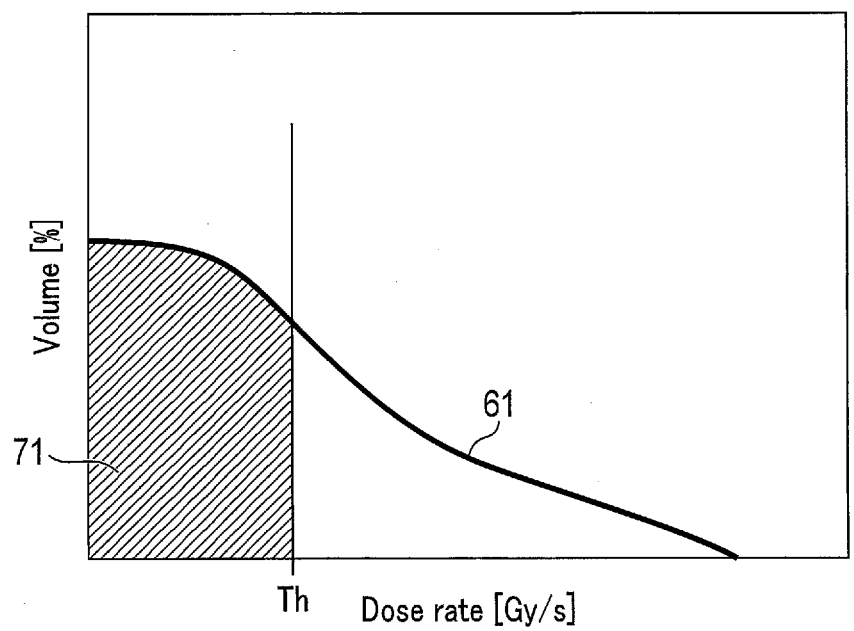
FIG. 6 is a diagram showing a normal irradiation volume ratio.

FIG. 6 is a diagram showing a normal irradiation volume ratio. As shown in FIG. 6, the processing circuitry 31 generates a frequency distribution (DrVH) 61 of the volume ratio (Volume[%]) of the predicted dose rate (Dose_rate[Gy/s]) in step SA6. The DrVH 61 is a graph in which the predicted dose rate is defined by the horizontal axis and the volume ratio is defined by the vertical axis. Next, the processing circuitry 31 sets a FLASH effect threshold Th to the DrVH. The FLASH effect threshold Th is defined by a predicted dose rate with which a therapeutic effect (FLASH effect) is achieved through FLASH irradiation. For example, the FLASH effect threshold Th is set to 40 Gy/s, for example. Preferably, the FLASH effect threshold Th is set for each organ. The processing circuitry 31 calculates the volume ratio 71 that is lower than the FLASH effect threshold as a normal irradiation volume ratio based on the DrVH generated in step SA6. The normal irradiation volume ratio 71 represents a volume ratio with which no FLASH effect can be achieved.

After step SA7, the processing circuitry 31 determines whether or not the irradiation conditions that have been set in step SA3 fall within acceptable ranges through the realization of the determination function 315 (step SA8). Specifically, the processing circuitry 31 determines whether or not the normal irradiation volume ratio calculated in step SA7 exceeds a predetermined determination threshold. The determination threshold is set to an upper limit of an acceptable normal irradiation volume ratio, for example. If the normal irradiation volume ratio calculated in step SA7 exceeds the determination threshold, the processing circuitry 31 determines that the irradiation conditions do not fall within the acceptable ranges. If the normal irradiation volume ratio calculated in step SA7 does not exceed the determination threshold, the processing circuitry 31 determines that the irradiation conditions fall within the acceptable ranges.

After step SA8, the processing circuitry 31 displays the normal irradiation volume ratio calculated in step SA7 and the determination result obtained in step SA8 through the realization of the display control function 316 (step SA9). In step SA9, the processing circuitry 31 causes the display device 33 to display the normal irradiation volume ratio and the determination result with a predetermined layout.

Figure 7:
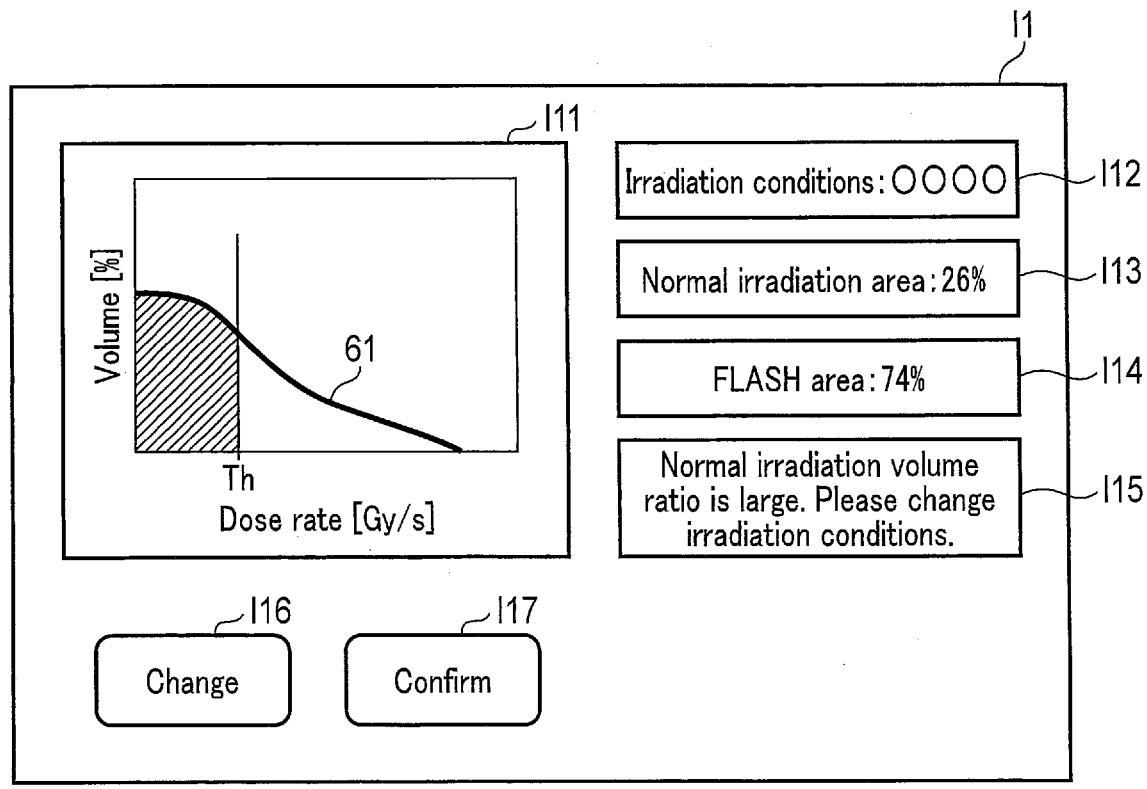
FIG. 7 is a diagram showing an example of a display window of a normal irradiation volume ratio and a determination result.

FIG. 7 is a diagram showing an example of the display window I1 of a normal irradiation volume ratio and a determination result. The display window I1 is displayed on the display device 33. As shown in FIG. 7, the display window I1 includes the display area I11 for the DrVH61, the display area I12 for the irradiation conditions, the display area I13 for the normal irradiation area, the display area I14 of the FLASH area, and the display area I15 for the determination result. The display area I11 displays the DrVH 61. In DrVH61, the normal irradiation volume ratio may be emphasized. The irradiation conditions are displayed in the display area I12. The display area I13 displays a numerical value (e.g., 26%) of a volume ratio of the normal irradiation area (normal irradiation volume ratio). The display area I14 displays a numerical value (e.g., 74%) of a volume ratio of the FLASH area. The volume ratio of the FLASH area can be calculated by reducing a normal irradiation volume ratio from 100%. The display area I15 displays a message corresponding to a determination result of the determination process performed in step SA8. For example, if it is determined in step SA8 that the irradiation conditions do not fall within the acceptable ranges, a message, such as "The normal irradiation volume ratio is too great" or "Change the irradiation conditions", is displayed.

After step SA9, the processing circuitry 31 determines whether the irradiation conditions should be changed or not through the realization of the determination function 315 (step SA10).

As shown in FIG. 7, the display window I1 displays the change button 116 and the confirmation button 117. The change button 16 is a GUI (graphical user interface) button for instructing the change of the irradiation conditions. The confirmation button 17 is a GUI button for instructing a confirmation of the irradiation conditions. The user checks the determination result and the normal irradiation volume ratio, etc. displayed on the display window I1, and when the user determines that the irradiation conditions ought to be changed, the user presses the change button 116 via the input device 34, etc. If the change button 116 is pressed, the processing circuitry 31 determines that the irradiation conditions are going to be changed in step SA10.

If it is determined that the irradiation conditions are going to be changed in step SA10 (Yes in step SA10), the processing circuitry 31 sets a new irradiation condition through the realization of the condition setting function 312 (step SA3). In other words, the processing circuitry 31 changes the parameter values of the irradiation conditions, such as the irradiation field, the application dose, and the exposure rate, etc. in accordance with a user's instruction via the input device 34 or a predetermined algorithm. The processing circuitry 31 may change the parameter values of the irradiation conditions in such a manner that the normal irradiation volume ratio becomes smaller, or in such a manner that the normal irradiation volume ratio becomes smaller than the determination threshold. For example, the processing circuitry 31 may determine a conditional expression representing a correspondence between the parameter values of the irradiation conditions and the normal irradiation volume ratio, and may calculate the parameter values of the irradiation conditions that minimize the normal irradiation volume ratio based on the conditional expression. Alternatively, the processing circuitry 31 may determine the parameters values of the irradiation conditions with which the normal irradiation volume ratio may take a minimum value by using a Gaussian progression model, such as a Bayes optimization, etc. Furthermore, the processing circuitry 31 may randomly change the parameter values of the irradiation conditions. Alternatively, the processing circuitry 31 may change the parameter values of the irradiation conditions to those designated by the user via the input device 34.

Figure 8:
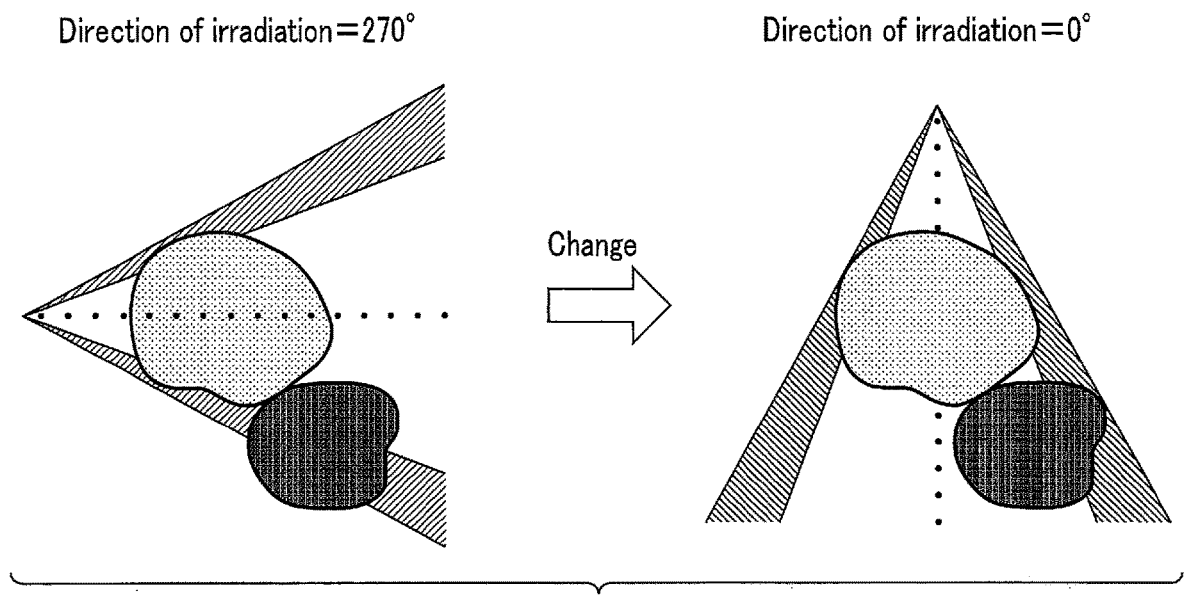
FIG. 8 is a diagram schematically showing a process of changing an irradiation condition.

FIG. 8 is a diagram schematically showing a process of changing the irradiation conditions. As shown in FIG. 8, if the irradiation direction is 270 degrees, the healthy tissue region RB is widely superimposed on the normal irradiation area R3 and the normal irradiation volume ratio is greater than the determination threshold. In this case, suppose it is determined in step SA8 that the irradiation conditions do not fall within the acceptable ranges. If the irradiation direction is 0 degree on the other hand, the healthy tissue area RB is superimposed on the normal irradiation area R3 only in a relatively small range. In this case, the processing circuitry 31 changes the irradiation direction from 270 degrees to 0 degree as shown in FIG. 8.

In step SA3, upon change of the irradiation conditions, the processing circuitry 31 performs steps SA4 to SA9 similarly to the above-described manner. In other words, the processing circuitry 31 calculates a volume index value based on the changed irradiation conditions to determine whether or not the changed irradiation conditions are acceptable based on the volume index value after the change of the irradiation conditions. In step SA9, the processing circuitry 31 may display the normal irradiation volume ratio calculated under the irradiation conditions that have been changed in step SA7 and the determination result in step SA8, or may display these information items together with the normal irradiation volume ratio under the irradiation conditions before the change.

Figure 9:
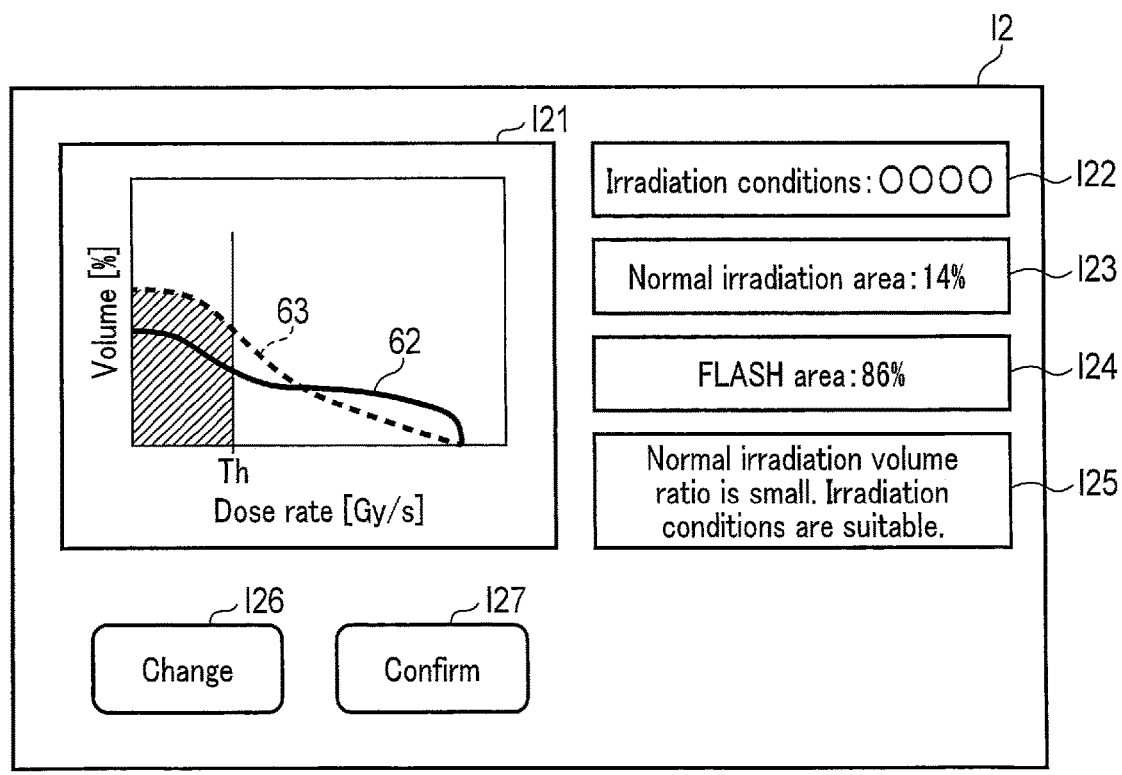
FIG. 9 is a diagram showing an example of a display window of a normal irradiation volume ratio and a determination result under a changed irradiation condition.

FIG. 9 is a diagram showing an example of the display window I2 of the normal irradiation volume ratio and the determination result under the changed irradiation conditions. As shown in FIG. 9, the display window I2 includes the display area I21 for the modified DrVH 62, the display area I22 for the irradiation conditions, the display area I23 for the normal irradiation area, the display area I24 for the FLASH area, the display area I25 for the determination result, the change button 126, and the confirmation button 127. The display area I22, the display area I23, the display area I24, the display area I25, the change button 126, and the confirmation button 127 are approximately the same as the display area I12, the display area I13, the display area I14, the display area I15, the change button 116, and the confirmation button 117 shown in FIG. 7, respectively.

As shown in FIG. 9, the display area I21 displays the DrVH 62 calculated under the changed irradiation conditions and the DrVH 61 calculated under the irradiation conditions before the change in a single graph. For example, the processing circuitry 31 displays the DrVH62 after the condition change and the DrVH61 before the condition change with different visual characteristics such as different line types and colors. The user observers the DrVH62 and DRVH61 after and before the condition change to understand the change in the normal irradiation volume ratio due to the change in the irradiation conditions. The display area I25 displays a message in accordance with a determination result of the determination process performed in step SA8. For example, if it is determined that the irradiation conditions are in acceptable ranges in step SA8, a message such as "the normal irradiation volume ratio is small" or "the irradiation conditions are valid", etc., is displayed.

After step SA9, the processing circuitry 31 determines whether the irradiation conditions should be changed or not through the realization of the determination function 315 (step SA10). The user checks the determination result and the normal irradiation volume ratio, etc. displayed on the display window I2, and when they determine that the irradiation conditions need not to be changed, the user presses the confirmation button 127 via the input device 34, etc. If the confirmation button 127 is pressed, the processing circuitry 31 determines that the irradiation conditions are not going to be changed in step SA10.

If it is determined that the irradiation conditions are not going to be changed in step SA10 (No in step SA10), the processing circuitry 31 sets, by the current irradiation condition through the realization of the condition setting function 312, the current irradiation conditions that have been set in step SA3 as a confirmed version (step SA11).

As described above, the processing circuitry 31 is able to search an optimal irradiation condition in which the normal irradiation volume ratio is smaller than a determination threshold by repeating the process from step SA3 to step SA10. The confirmed irradiation conditions are stored in the storage apparatus 32 and sent to the radiotherapy apparatus 4 and the radiotherapy support apparatus 5.

After step SA11, the therapy planning process by the radiotherapy planning apparatus 3 is finished. Thereafter, the radiotherapy apparatus 4 irradiates the patient with radiation in accordance with the confirmed irradiation conditions to conduct radiotherapy.

The flow of the therapy planning process shown in FIG. 3 is merely an example, and the flow can be modified in various ways, without being limited to this example. A few modifications are described hereinafter.

In the foregoing example of the process, whether the irradiation conditions should be changed or not is determined in step SA10. However, the present embodiment is not limited thereto. For example, if it is determined in step SA8 that the irradiation conditions do not fall within the acceptable ranges, the processing circuitry 31 may assume that the irradiation conditions should be changed; if it is determined that the irradiation conditions fall within the acceptable ranges in step SA8 on the other hand, the processing circuitry 31 may assume that the irradiation conditions should not be changed.

In the foregoing example of the process, the frequency distribution of the predicted dose rate (DrVH) is generated (step SA6) and displayed (step SA9). However, the present embodiment is not limited thereto. For example, the processing circuitry 31 may generate a frequency distribution of a predicted dose (DVH) of each of the FLASH area and the normal irradiation area that are set in step SA4 and display the distributions on the display device 33.

Figure 10:
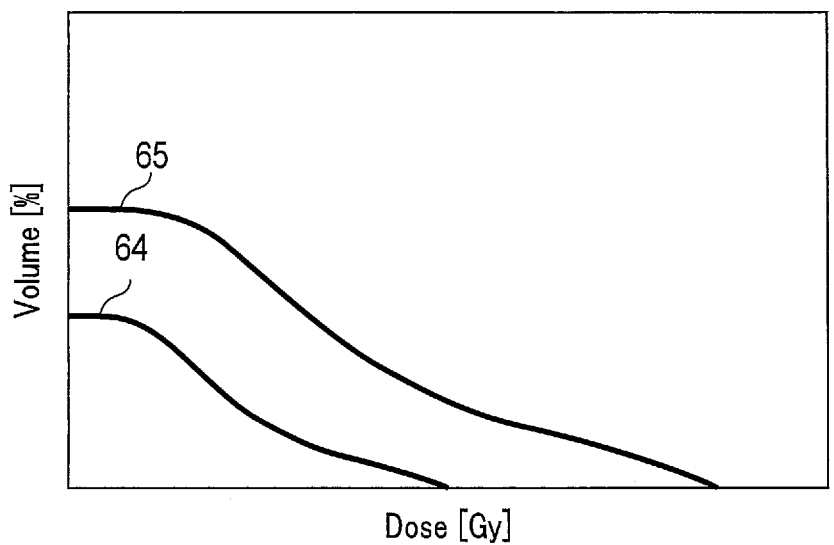
FIG. 10 is a diagram showing a display example of a DVH of a FLASH area and a DVH of a normal irradiation area.

FIG. 10 is a diagram showing a display example of a DVH 64 of a FLASH area and a DVH 65 of a normal irradiation area. As shown in FIG. 10, the DVH 64 and the DVH 65 are a graph in which the predicted dose (Dose[Gy]) is defined by the horizontal axis and the volume ratio (Volume[%]) is defined by the vertical axis. With the DVH displayed, the user is able to check a total amount of irradiation dose applied to the patient separately in each of the FLASH area and the normal irradiation area. The processing circuitry 31 may generate and display a DVH of a sum of the FLASH area and the normal irradiation area. It is thereby possible for a user to compare the FLASH area to the sum area (whole area) and/or a DVH of the normal irradiation area.

If a plurality of healthy portions of tissues (organs), such as a heart or a stomach, etc. are included in an irradiation field, the processing circuitry 31 may generate and display a DrVH and/or DVH for each healthy tissue portion, or may calculate and display a normal irradiation volume ratio for each healthy tissue portion. In this case, the processing circuitry 31 may display a DrVH and/or DVH of a particular organ only, or a plurality of DrVHs and/or a plurality of DVHs of a plurality of organs. The processing circuitry 31 may display the DrVH and the normal irradiation volume ratio of each organ in either a graph as shown in FIG. 6, etc. or a numerical value. The generation and display of a DrVH for each organ, or the calculation and display of a normal irradiation volume ratio, allows the user to closely distinguish between an area in which a FLASH effect is achieved and an area with no FLASH effect. The processing circuitry 31 may display a DrVH in the case where all healthy organs are in a single area, along with a DrVH of each organ.

As described above, the radiotherapy planning apparatus 3 according to the first embodiment includes the processing circuitry 31. The processing circuitry 31 sets irradiation conditions of irradiation. The irradiation conditions include at least a radiation field and an application dose index value that are set for a medical image. The processing circuitry 31 calculates, based on irradiation conditions, a volume index value of an area in the healthy tissue included in the radiation field and relating to a predicted dose index value that falls below the FLASH effect threshold. The processing circuitry 31 determines whether or not the irradiation conditions are accepted based on the volume index value.

According to the above configuration, it is possible to determine whether or not the irradiation conditions are acceptable in accordance with a volume index value of an area to which a FLASH effect can be achieved in healthy tissue. It is thereby possible to search for irradiation conditions with which a volume index value of an area to which a FLASH effect cannot be achieved is relatively small. It is thereby possible to perform radiotherapy safely with high accuracy, which leads to a reduction of events harmful to healthy issue in an ultra-high dose-rate, short radiation method, such as a FLASH radiotherapy, etc.

In the above-described example of the process, the processing circuitry 31 determines that the irradiation conditions are not in acceptable ranges if the volume index value of an area in which the value falls below a FLASH effect threshold exceeds a determination threshold. However, the present embodiment is not limited thereto. For example, the processing circuitry 31 may assume that a normal irradiation area can be recognized as an area to which a FLASH effect cannot be achieved, and may determine that the volume index value of the normal irradiation area specified in step SA3 exceeds a threshold, and determine that the irradiation conditions are not in allowable ranges if the volume index value of a normal irradiation area falls below the threshold. It is thereby possible to determine the suitability of the irradiation conditions simply based on a volume index value of an area with a low possibility of having a FLASH effect.

The processing circuitry 31 of the radiotherapy planning apparatus 3 according to the first embodiment performs a setting process, an acquisition process, an evaluation process, and an output process in different aspects. In the setting process, the processing circuitry 31 sets irradiation conditions for a medical image relating to a patient. The irradiation conditions include an irradiation field, a total dose, a dose rate, and the like, and are set by the condition setting function 312. In the acquisition process, the processing circuitry 31 acquires a histogram (DrVH) of a radiation dose rate in a predetermined area in the patient based on the irradiation conditions. The irradiation conditions include an irradiation field, a total dose, a dose rate, and the like, and are set by the condition setting function 312. As a method of acquiring a DrVH, the processing circuitry 31 of the radiotherapy planning apparatus 3 may generate a DrVH or another computer may generate a DrVH. In the latter case, the processing circuitry 31 receives a DrVH from a computer that generates the DrVH or a computer that stores the DrVh, via the communication device 35. The predetermined area is either an irradiation field or an organ, a healthy area, and/or an organ-at-risk included in an irradiation field. In the evaluation process, the processing circuitry 31 evaluates the irradiation conditions based on the DrVH. In the output process, the processing circuitry 31 outputs information based on an evaluation result of the irradiation conditions. The information that is output from the processing circuitry 31 may be displayed on the display device 3, stored in the storage apparatus 32, or transferred to another computer via the communication device 35.

According to the above configuration, since the irradiation conditions are determined based on a DrVH, which is a frequency distribution of a predicted dose rate, it is therefore possible to easily and simply determine the suitability of the irradiation conditions regarding a FLASH irradiation method.

In the evaluation process, the processing circuitry 31 may determine the suitability of the irradiation conditions based on a DrVH. Specifically, the processing circuitry 31 determines the suitability of the irradiation conditions based on a comparison of the volume ratio of an irradiation area (FLASH area) to a DrVH in either a first area from which an irradiation effect of FLASH cannot be obtained (a normal irradiation area) or a second area from which FLASH cannot be obtained with a first threshold (determination threshold). Specifically, if the volume ratio of a normal irradiation area of a radiation area is larger than a first determination threshold, it is determined that the irradiation conditions are not suitable; if the volume ratio is smaller than the first determination threshold, it is determined that the irradiation conditions are suitable. If the volume ratio of a FLASH area of a radiation area is larger than a second determination threshold, it is determined that the irradiation conditions are suitable; if the volume ratio is smaller than the second determination threshold, it is determined that the irradiation conditions are not suitable. The processing circuitry 31 does not necessarily determine the suitability of the irradiation conditions. For example, the processing circuitry 31 may cause the display device 33 to display a DrVH and a determination threshold. The user is thereby able to estimate a volume ratio of the normal irradiation area or the FLASH area and determine the suitability of the irradiation conditions, by checking the location of the determination threshold in the DrVH.

The processing circuitry 31 according to the first embodiment may further perform a specifying process. In the specifying process, the processing circuitry 31 specifies a normal irradiation area and a FLASH area in a medical image or a DrVH relating to a predetermined area.

In the specifying process, the processing circuitry 31 specifies a penumbra area in the predetermined area as a normal irradiation area and specifies an area other than the penumbra area in the predetermined area as a FLASH area. As an example, the processing circuitry 31 specifies a penumbra area and a non-penumbra area by a user's area designation that targets the predetermined area in the medical image. As another example, the processing circuitry 31 specifies a penumbra area by a user's area designation that targets the predetermined area in the medical image and specifies the area other than the penumbra area in the predetermined area as a non-penumbra area. As another example, the processing circuitry 31 specifies a non-penumbra area by a user's area designation targeting the predetermined area in the medical image, and specifies a penumbra area other than the non-penumbra area in the predetermined area. As another example, the processing circuitry 31 may specify a penumbra area and a non-penumbra area in the predetermined area of the medical image based on a parameter defining an irradiation field.

In the specifying process, the processing circuitry 31 may specify a normal irradiation area and a FLASH area based on at least one of an irradiation depth of radiation in the irradiation area, irradiation absorption characteristics of tissue in the irradiation area, and a penumbra in the irradiation area. The irradiation depth means a distance from a body surface along the irradiation direction. Specifically, the processing circuitry 31 specifies a penumbra area and a non-penumbra area in the irradiation area in the medical image with the above method. Next, the processing circuitry 31 calculates a predicted dose rate for each pixel in the irradiation area based on the irradiation conditions. At this time, the processing circuitry 31 calculates, for the penumbra area, a predicted dose rate in consideration of the attenuation of the radiation due to a penumbra. The processing circuitry 31 calculates a predicted dose rate in consideration of at least one of the attenuation rate of radiation according to the irradiation depth in the irradiation area or the attenuation rate of the radiation according to the radiation absorption characteristics of tissue. For the attenuation rate according to the irradiation depth and the radiation absorption characteristics of tissue, experimentally determined values or values calculated by prediction may be used. The processing circuitry 31 identifies an area in which the predicted dose rate falls below a FLASH effect threshold as a normal irradiation area, and identifies an area in which the predicted dose rate exceeds a FLASH effect threshold as a FLASH area.

In the specifying process, the processing circuitry 31 may specify a normal irradiation area and a FLASH area in a DrVH based on the DrVH and a FLASH effect threshold. As an example, the processing circuitry 31 identifies, as a normal irradiation area, an area in which the predicted dose rate falls below a FLASH effect threshold in a DrVH, and identifies, as a FLASH area, an area in which the predicted dose rate exceeds a FLASH effect threshold. In this case, a normal irradiation area and a FLASH area are not necessarily specified in a medical image.

In the determination process, the processing circuitry 31 may determine the suitability of the irradiation conditions based on a comparison of a predicted dose for tissue in a normal irradiation area with a tolerable dose for the tissue. The determination of the suitability of the irradiation conditions using the tolerable dose is performed, for example, after the irradiation conditions are determined to be suitable in the determination of suitability using a DrVH. The tolerable dose is an amount of radiation that a targeted tissue portion can tolerate. The tolerable dose differs between tissues. As an example, the processing circuitry 31 specifies a tolerable dose of tissue present in a normal irradiation area using a tolerable dose table. The tolerable dose table is a lookup table (LUT) recording tolerable doses according to tissue types. The type of tissue means an anatomical name or a symbol of tissue. The processing circuitry 31 specifies a type of tissue present in the normal irradiation area using an anatomical landmark, etc., and specifies a tolerable dose for the tissue by searching the tolerable dose table using the specified type of tissue as a search key. The processing circuitry 31 generates a spatial distribution of a predicted dose. The processing circuitry 31 specifies tissue as a target for the process in the normal irradiation area, and specifies a predicted dose rate of the tissue by referring to the spatial distribution of a predicted dose, and compares the specified predicted dose with the tolerable dose for the tissue. If the predicted dose exceeds the tolerable dose, the irradiation conditions are determined to be unsuitable; if the predicted dose falls below the tolerable dose, the irradiation conditions are determined to suitable. According to the determination process, the suitability of the irradiation conditions is determined using not only a volume ratio of the normal irradiation area and/or the FLASH area but also the tolerable dose; thus, it is possible to further reduce unnecessary radiation that healthy tissue is exposed to. The determination of the suitability of the irradiation conditions using a tolerable dose may be performed in place of the determination of the suitability of the irradiation conditions using a DrVH.

In the output process, the processing circuitry 31 causes the display device 33 to display information based on the suitability of the irradiation conditions. The information based on the suitability of the irradiation conditions may be information indicating that the irradiation conditions are suitable, information indicating that the irradiation conditions are not suitable, information prompting radiotherapy to start based on the suitability of the irradiation conditions, and information prompting changes of the irradiation conditions based on the unsuitability of the irradiation condition. Information indicating that the irradiation conditions are suitable is, for example, "The normal irradiation volume ratio is small. The irradiation conditions are suitable." displayed in the display section I25, as illustrated in FIG. 9. Information prompting the change of the irradiation conditions is, for example, "The normal irradiation volume ratio is large. Please change the irradiation conditions." displayed in the display area I15, as illustrated in FIG. 7.

In the output process, the processing circuitry 31 causes the display device 33 to display the normal irradiation area and the FLASH area in a distinguishable manner. As an example, the processing circuitry 31 display the normal irradiation area (the shaded area) and the FLASH area (the area in white) in DrVH in a visually distinguishable manner as shown in FIG. 7. At this time, the processing circuitry 31 may put a mark on the DrVH to indicate a determination threshold. For example, a boundary line indicating the determination threshold Th of FIG. 7 is displayed as the mark. As an example, the processing circuitry 31 may display the normal irradiation area and the FLASH area in the medical image in a visually distinguishable manner.

In the output process, the processing circuitry 31 may cause the display device 33 to display a numerical value indicating a volume ratio(s) of the normal irradiation area and/or the FLASH area. For example, as shown in FIG. 7, the processing circuitry 31 may display both "26%", which is a numerical value indicating the volume ratio of the normal irradiation area, and "74%", which is a numerical value indicating the volume ratio of the FLASH area.

Second Embodiment

Figure 11:
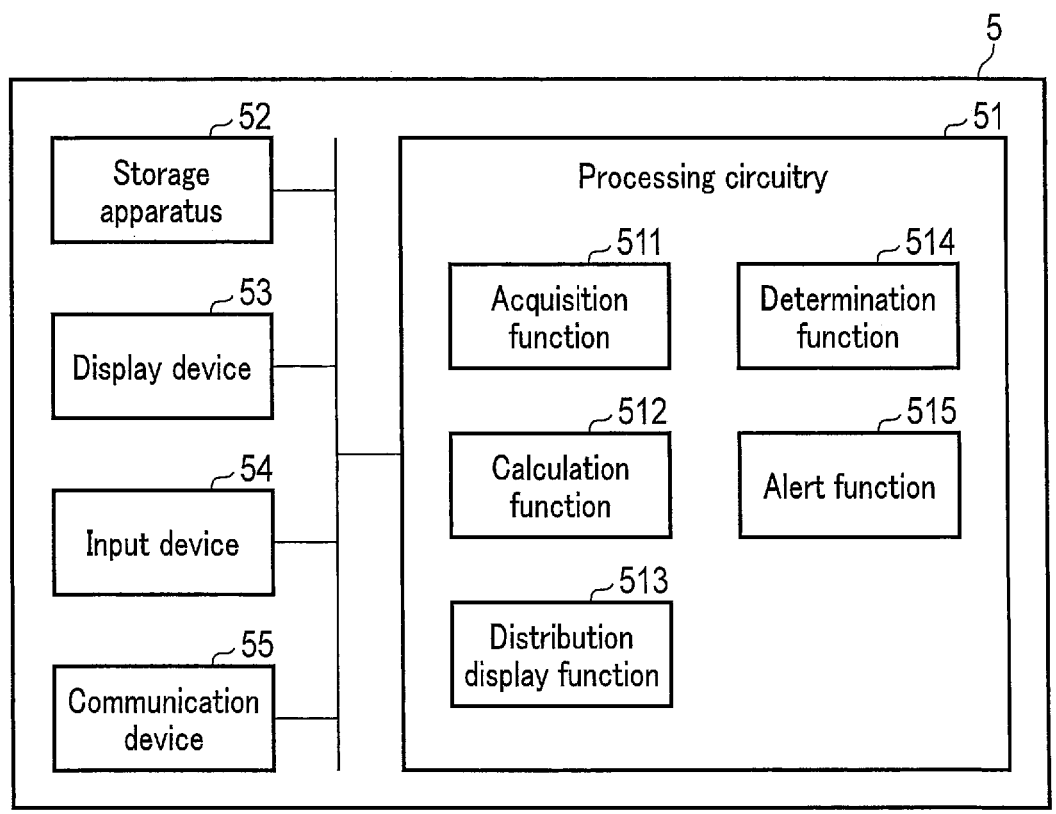
FIG. 11 is a diagram showing a configuration example of a radiotherapy support apparatus according to a second embodiment.

FIG. 11 is a diagram showing a configuration example of a radiotherapy support apparatus 5 according to the second embodiment. The radiotherapy support apparatus 5 includes processing circuitry 51, a storage apparatus 52, a display device 53, an input device 54, and a communication device 55.

The processing circuitry 51 has a processor such as a CPU and a GPU. When the processor activates a radiotherapy planning program installed onto the storage apparatus 32, etc., the processor realizes the acquisition function 511, the calculation function 512, the distribution display function 513, the determination function 514, and the alert function 515. Note that the embodiment is not limited to the case in which the respective functions 511 to 515 are realized by a single processing circuitry. Processing circuitry may be composed by combining a plurality of independent processors, and the respective processors may execute programs, thereby realizing the functions 511 to 515.

By the realization of the acquisition function 511, the processing circuitry 51 acquires various information items. For example, the processing circuitry 51 acquires data of a predicted dose rate frequency distribution (DrVH) and a normal irradiation volume ratio received from the radiotherapy planning apparatus 3.

By the realization of the calculation function 512, the processing circuitry 51 calculates a positional deviation of a patient laid on a treatment bed of the radiotherapy apparatus 4. Specifically, the processing circuitry 51 calculates a positional deviation between the current position of a patient laid on the bed of the radiotherapy apparatus 4 and a reference position.

By the realization of the distribution display function 513, the processing circuitry 51 displays the frequency distribution (DrVH) of the predicted dose index value relating to the current position and the frequency distribution (DrVH) of the predicted dose index value relating to the reference position. For example, the processing circuitry 51 causes the display device 53 to display the DrVH relating to the current position and the DrVH relating to the reference position.

By the realization of the determination function 514, the processing circuitry 51 determines whether or not the positional deviation calculated by the calculation function 512 is acceptable based on a comparison between the volume index value and the reference volume index value of an area in the healthy tissue of the patient corresponding to the current position and relating to the predicted dose index value that falls below the first threshold. The reference volume index value is a volume index value of an area in the healthy tissue of the patient corresponding to the reference position and relating to the predicted dose index value that falls below the first threshold. It suffices that a normal irradiation volume ratio in the first embodiment is used as a volume index value of an area relating to the predicted dose index value that falls below the first threshold. The first threshold is set to a FLASH effect value according to the first embodiment.

By the realization of the alert function 515, the processing circuitry 51 gives an alert if it is determined that the positional deviation is not acceptable for the determination function 514. The alert may be given as either an alert message via the display device 53 or an alert sound through a speaker.

The storage apparatus 52 is a memory apparatus such as a ROM, a RAM, an HDD, an SSD, or an integrated circuit storage unit, etc., configured to store various kinds of information. The storage apparatus 52 may be not only the above-listed memory apparatuses, but also a driver that writes and reads various types of information in and from, for example, a portable storage medium such as a CD, a DVD, or a flash memory, or a semiconductor memory. The storage apparatus 52 may be provided in an external computer connected to the radiotherapy support apparatus 5 via a network. For example, the storage apparatus 52 stores a therapy support program, etc.

The display device 53 displays various types of information. As the display device 53, for example, a liquid crystal display, a CRT display, an organic EL display, a plasma display, or any other display may be used as appropriate. The display device 53 may be a projector.

The input device 54 accepts various kinds of input operations from a user, converts the accepted input operations to electric signals, and outputs the electric signals to the processing circuitry 51. Specifically, as the input device 54, a mouse, a keyboard, a trackball, a switch, a button, a joystick, a touchpad, a touch panel display, etc. can be used as appropriate. The input device 34 outputs electrical signals to the processing circuitry 51 according to an input operation. The input device 54 may be a speech recognition device that converts audio signal collected by a microphone into command signals. The input device 54 may be an input device provided in an external computer connected to the system via a network, etc.

The communication device 55 is an interface for data communication with other apparatuses included in the radiotherapy system 1. For example, the communication device 55 acquires data of a predicted dose rate frequency distribution (DrVH) and a normal irradiation volume ratio received from the radiotherapy planning apparatus 3.

Next, an operation example of the radiotherapy support apparatus 5 is explained. Suppose a medical image in the following explanations is a three-dimensional medical image collected by an X-ray computed tomography apparatus.

Figure 12:
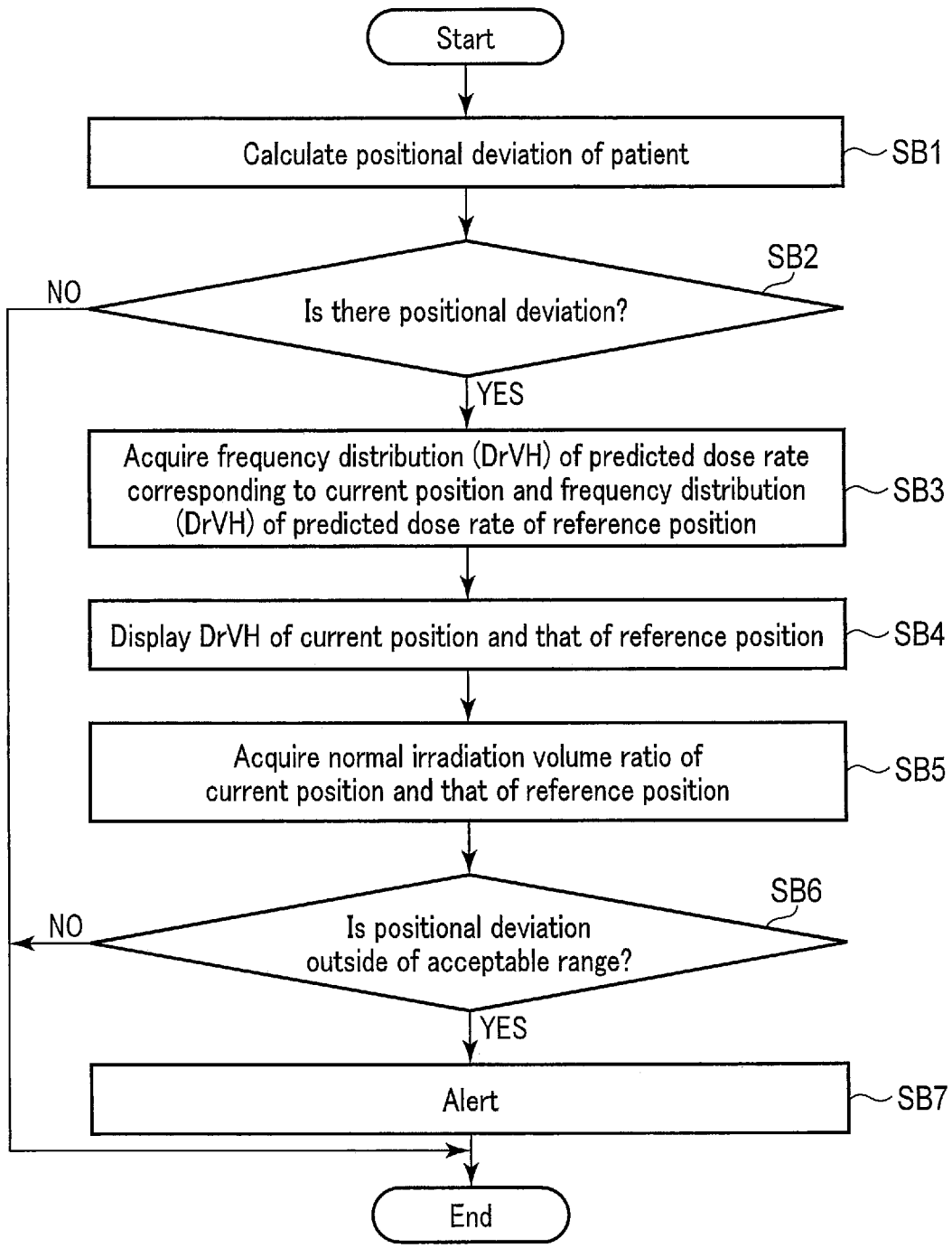
FIG. 12 is a diagram showing a typical flow of a therapy support process in the radiotherapy support apparatus.

FIG. 12 is a diagram showing a typical flow of a therapy support process in the radiotherapy support apparatus 5.

As shown in FIG. 12, the processing circuitry 51 calculates a positional deviation of a patient by the realization of the positional deviation calculation function 512 (step SB1). In step SB1, the processing circuitry 51 calculates a positional deviation between a current position of the patient and a reference position. It suffices that the current position of the patient may be obtained with a discretionarily selected method. For example, the user performs optical scanning on the patient laid on the bed using a shape measuring apparatus, which is an application of three-dimensional optical scanning. The shape measuring apparatus generates a graphical model relating to an appearance of the patient (hereinafter, "patient model") based on scan data, which is series data of position information of sample points. The patient model at the current position is stored in the storage apparatus 52 of the radiotherapy support apparatus 5. The storage apparatus 52, on the other hand, stores a pre-generated patient model of the reference position. The reference position is a patient position when a therapy plan was made. In other words, the reference position is a position of a patient at the time medical images for therapy planning were collected.

The processing circuitry 51 arranges the patient model at the current position and the patient model of the reference position on the same image processing coordinate system and calculates a positional deviation between the patient model at the current position and the patient model of the reference position. The positional deviation is defined by a direction (hereinafter, a "direction of positional deviation) and a distance (hereinafter, an "amount of positional deviation"). The direction of positional deviation is expressed by the craniocaudal direction, left-to-right direction, and anteroposterior direction of the patient's head. The amount of positional deviation is defined by a distance from the reference position. The calculation of the positional deviation is performed as follows. First, the processing circuitry 51 specifies the same anatomical references for the patient model of a current position and a patient model of the reference positon, and calculates a direction of positional deviation and an amount of positional deviation from the anatomical reference for the patient model of the reference position and the anatomical reference for the patient model of the current position.

After step SB1, the processing circuitry 51 determines whether or not there is a positional deviation with the realization of the positional deviation calculation function 512 (step SB2). In step SB2, the processing circuitry 51 compares the amount of positional deviation calculated in step SB1 with a threshold. The threshold is set to a discretionarily determined value, such as 0. The processing circuitry 51 determines that there is no positional deviation when the positional deviation falls below the threshold (No in step SB2). In this case, the therapy support processing indicated in FIG. 12 is finished. If the amount of positional deviation exceeds a threshold, the processing circuitry 51 determines that there is a positional deviation.

When it is determined in step SB2 that there is a positional deviation (Yes in step SB2), the processing circuitry 51 acquires, through the realization of the acquisition function 511, a frequency deviation (DrVH) of a predicted dose rate corresponding to a current position and a frequency deviation (DrVH) of a predicted dose rate corresponding to a reference position (step SB3).

FIG. 13 is a diagram schematically showing a series of processes relating to the acquisition of a DrVH of the current position and a DrVH of the reference position. As shown in FIG. 13, the reference position and the current position of the patient are acquired. Suppose the current position deviates from the reference position by 3 cm in the caudal direction. In step SB1, a positional deviation between the reference position and the current position is calculated. In the case of FIG. 13, the positional deviation is in the caudal direction, and the amount of the deviation is 3 cm.

In step SB3, the storage apparatus 32 stores a DrVH and a normal irradiation volume ratio associated for respective combinations of a direction of positional deviation and an amount of positional deviations. The DrVH and the normal irradiation volume ratio of each combination is generated and calculated in advance for each combination by the radiotherapy planning apparatus 3. For example, the processing circuitry 31 of the radiotherapy planning apparatus 3 generates and calculates the DrVH and the normal irradiation volume ratio when the patient's organ is shifted at predetermined intervals with respect the craniocaudal direction, the left- to right direction, and the anteroposterior direction. The DrVH and the normal irradiation volume ratio is calculated and based on the confirmed irradiation conditions.

As shown in FIG. 13, if it is determined in step SB2 that there is a positional deviation, the DrVH of the reference position and the DrVH of the current positon are acquired from the storage apparatus 52. In the case of FIG. 13, a DrVH at the position at 3 cm from the reference position with respect to the caudal direction, is obtained as a DrVH of the current position.

After step SB3, the processing circuitry 51 that enables the distribution display function 513 displays the DrVH of the current position and the DrVH of the reference position acquired in step SB3 (step SB4). In step SB4, the processing circuitry 51 causes the display device 53 to display the DrVH of the current position and the DrVH of the reference position in a predetermined layout.

Figure 14:
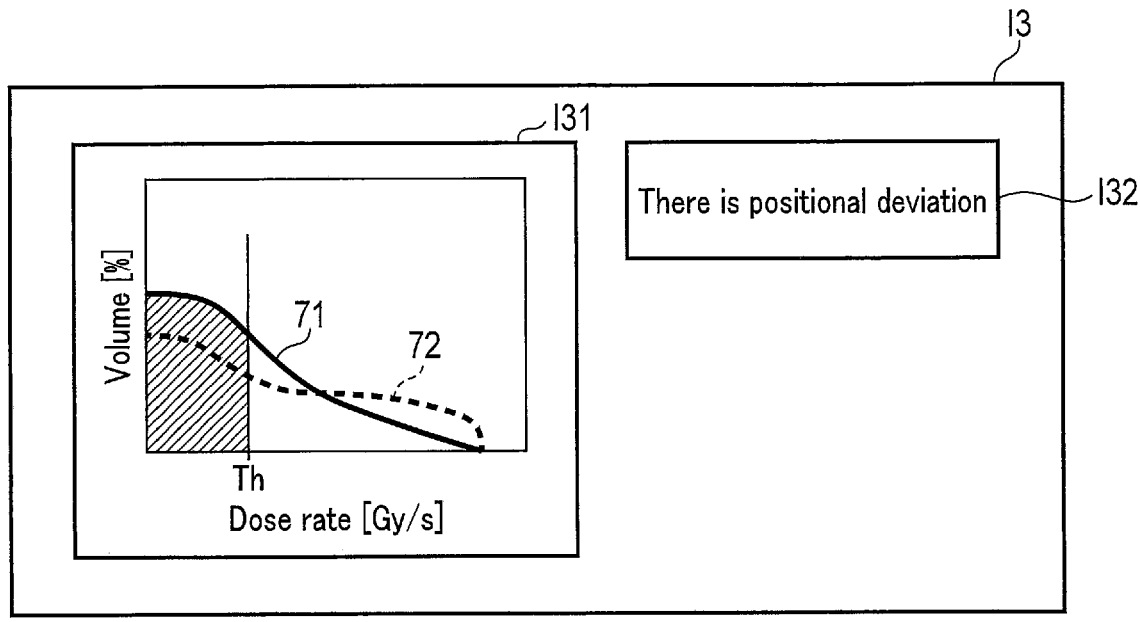
FIG. 14 is a diagram schematically showing a display window of a DrVH of a current position and a DrVH of a reference position.

FIG. 14 is a diagram showing the display window I3 for the DrVH of the current position and the DrVH of the reference position. The display window I3 is displayed on the display device 53. As shown in FIG. 14, the display window I3 includes the display area I31 for the DrVH and the display area I32 for the message. The display area I31 shows the DrVH 71 of the current position and the DrVH 72 of the reference position. Displaying the DrVH 71 of the current position and the DrVH 72 of the reference position allows the user to infer damage caused by radiation of a dose rate lower than a FLASH effect threshold applied to the healthy tissue at the current position in comparison with the reference position. The DrVH 71 of the current position and the DrVH 72 of the reference position corresponding to a current position are displayed with different visual aspects, for example different lines and colors. The display area I32 displays a message in accordance with a result of determination regarding a presence/absence of the positional deviation in step SB2. For example, if it is determined in step SB2 that there is a positional deviation, a message indicating that the presence of a positional deviation, such as "A positional deviation occurs", is displayed as shown in FIG. 14.

After step SB4, the processing circuitry 51 acquires a normal irradiation volume ratio of the current position and a normal irradiation volume ratio of the reference position by the realization of the acquisition function 511 (step SB5). In step SB5, the processing circuitry 51 acquires, from the storage apparatus 52 storing a normal irradiation volume ratio of each of the combinations of a direction of positional deviation and an amount of positional deviation, a normal irradiation volume ratio of the current position and a normal irradiation volume ratio of the reference position.

After step SB5, the processing circuitry 51 determines whether or not the positional deviation calculated in step SB1 falls within an acceptable range through the realization of the determination function 514 (step SB6). In step SB6, if the amount of positional deviation exceeds a predetermined threshold, the processing circuitry 51 determines that the positional deviation falls within an acceptable range; if the amount of positional deviation falls below the predetermined threshold, the processing circuitry 51 determines that the positional deviation does not fall within the acceptable range. The threshold can be set at a discretionarily determined value. The threshold may be set at a different value in accordance with the direction of positional deviation.

If it is determined in step SB6 that the positional deviation falls within the acceptable range (Yes in step SB6), the processing circuitry 51 gives an alert by the realization of the alert function 515 (step S7). In step SB7, the processing circuitry 51 causes the display device 53 to display the alert window with a predetermined layout.

Figure 15:
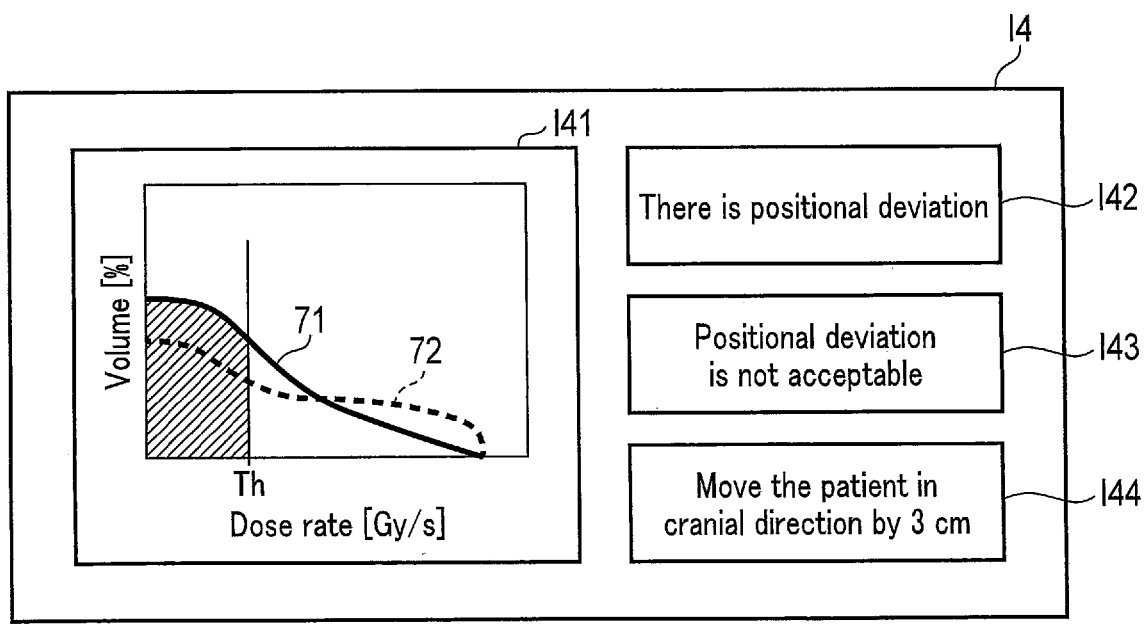
FIG. 15 is a diagram showing an example of an alert window.

FIG. 15 is a diagram showing an example of the alert window I4 example of an alert window. The alert window I4 is displayed on the display device 53. As shown in FIG. 15, the alert window I4 includes a display area I41 for DrVH, a first display area I42, a second display area I43, and a third display area I44. The display area I41 for DrVH and the first display area I42 are the same as the display area I31 and the display area I32 in FIG. 14, respectively.

As shown in FIG. 15, a message in accordance with a result of determination in step SB6 regarding whether or not the positional deviation falls under the acceptable range is displayed in the second display area I43. For example, if it is determined in step SB6 that the positional deviation does not fall within the acceptable range, an alert message, such as "A positional deviation is not acceptable", etc., is displayed. The third display area I44 displays a message indicating a direction and an amount of correction of the positional deviation. The direction and amount of correction of the positional deviation are calculated based on the direction and amount of the positional deviation between the reference position and the current position calculated in step SB1. Specifically, the direction of correction is defined as a direction of the positional deviation from the current position to the reference position, and the amount of correction is defined as an amount of the positional deviation from the current position to the reference position. For example, as shown in FIG. 13, the positional deviation between the reference position and the current position is 3 cm in the caudal direction, the direction of correction is the cranial direction, and an amount of correction is 3 cm. As the direction of correction and the amount of correction are thus displayed, the user can move the patient from the current position to the reference position.

The display of the direction of correction and the amount of correction is not limited to the means of displaying them as a message on the alert window I4 as shown in FIG. 15. For example, if a projector is available to serve as the display device 53, the direction of correction and the amount of correction may be projected onto the body surface of the patient.

FIG. 16 is a diagram showing a projection example of a direction of correction and an amount of correction. As shown in FIG. 16, the patient P is laid on the bed 41 of the radiotherapy apparatus 4. The patient P is laid at a current position deviated from the reference position by 3 cm in the caudal direction, as shown in FIG. 12. In this case, a direction of correction and an amount of correction are a cranial direction and 3 cm, respectively. The projector, which serves as the display device 53, projects a projection image 15 showing the direction of correction and the amount of correction on the body surface of the patient P. The projected image 15 consists of a marking indicating the direction of correction and a value indicating the amount of correction. Specifically, an arrow indicating the cranial direction is projected as the marking indicating the direction of correction, and a value, such as "3 cm", indicating the amount of correction is projected, superposed on the arrow. Thus, by projecting the direction of correction and the amount of correction on the body surface of the patient, the user is able to know the direction of correction and the amount, without moving the line of sight to the display.

After step SB7, the therapy planning process by the radiotherapy support apparatus 5 is finished. After the therapy support process, radiotherapy is performed on the patient by the radiotherapy apparatus 4.

The flow of the therapy support process shown in FIG. 12 is merely an example, and the flow can be modified in various ways, without being limited to this example. A few modifications are described hereinafter.

In the above example of the process, the processing circuitry 51 acquires a DrVH in step SB3 and displays the DrVH in step SB4; however, the processing may acquire a DVH in step SB3 and display the DVH in step SB4.

As described above, the radiotherapy support apparatus 5 according to the second embodiment includes the processing circuitry 51. The processing circuitry 51 calculates a positional deviation between the current position of a patient laid on the bed of the radiotherapy apparatus 4 and a reference position. The processing circuitry 51 determines whether or not the positional deviation is acceptable based on a comparison of a volume index value of an area relating to a predicted dose index value that falls below a FLASH effect value in healthy tissue of the patient corresponding to the current position (normal irradiation volume ratio) with a reference volume index value. If it is determined that the positional deviation is not acceptable, the processing circuitry 51 gives an alert.

According to the above configuration, the processing circuitry 51 determines whether or not the positional deviation of the patient is acceptable or not in accordance with a normal irradiation volume ratio of healthy tissue; it is thus possible to evaluate the suitability of the positional deviation of the patient in accordance with a volume amount which brings a FLASH effect to the healthy tissue.

According to at least one embodiment described above, it is possible to reduce events harmful to healthy tissue caused by radiotherapy.

The term "processor" used in the above explanation indicates, for example, a circuit, such as a CPU, a GPU, or an Application Specific Integrated Circuit (ASIC), and a programmable logic device (for example, a Simple Programmable Logic Device (SPLD), a Complex Programmable Logic Device (CPLD), and a Field Programmable Gate Array (FPGA)). The processor realizes its function by reading and executing the program stored in the storage circuitry. The program may be directly incorporated into the circuit of the processor instead of being stored in the storage circuit. In this case, the processor implements the function by reading and executing the program incorporated into the circuit. The function corresponding to the program may be realized by a combination of logic circuits, not by executing the program. Each processor of the present embodiment is not limited to a case where each processor is configured as a single circuit; a plurality of independent circuits may be combined into one processor to realize the function of the processor. Further, a plurality of components shown in FIG. 1, FIG. 2 and FIG. 11 may be integrated into one processor to achieve their functions.

While certain embodiments have been described, these embodiments have been presented by way of example only, and are not intended to limit the scope of the inventions. Indeed, the embodiments described herein may be embodied in a variety of other forms; furthermore, various omissions, substitutions, changes, and combinations of embodiments in the form of the embodiment described herein may be made without departing from the spirit of the invention. The accompanying claims and their equivalents are intended to cover such forms or modifications as would fall within the scope and spirit of the invention.

Regarding the foregoing embodiments, the appendage of the following is disclosed as one aspect and set of selective features of the invention.

(1)

A radiotherapy planning apparatus comprising processing circuitry configured to:
    set irradiation conditions for a medical image relating to a patient;
    acquire a histogram of a radiation dose rate in a predetermined area in the patient based on the irradiation conditions;
    evaluate the irradiation conditions based on the histogram; and
    output information based on an evaluation result of the irradiation conditions.

(2)

The processing circuitry may determine suitability of the irradiation conditions based on the histogram.

(3)

The processing circuitry may determine the suitability of the irradiation conditions based on a comparison between a first threshold and a volume ratio in the histogram of a first area or a second area to the irradiation area. The first area does not respond to a FLASH irradiation effect. The second area responds to a FLASH irradiation effect. The FLASH irradiation is a technique for selectively damaging a tumor without damaging healthy tissue by radiation at an ultra-high dose-rate (for example, 40 Gy/sec) for a short time (for example, 1 second or shorter).

(4)

The processing circuitry specifies the first area and the second area in a medical image or the histogram relating to the determined area.

(5)

The processing circuitry may specify a penumbra area in the predetermined area as the first area and specify an area other than the penumbra area in the predetermined area as the second area.

(6)

The processing circuitry may specify the first area and the second area based on at least one of an irradiation depth of radiation in the irradiation area, radiation absorption characteristics of tissue in the irradiation area, and a penumbra in the irradiation area.

(7)

The processing circuitry specifies the first area and the second area based on the histogram and a second threshold relating to the dose rate.

(8)

The processing circuitry may determine the suitability of the irradiation conditions based on a comparison between a predicted dose applied to tissue in a first area from which no FLASH irradiation effect can be obtained and a tolerable dose.

(9)

The processing circuitry may cause the display device to display information based on the suitability of the irradiation conditions.

(10)

If it is determined that the irradiation conditions are not suitable, the processing circuitry may display information based on the suitability of the irradiation conditions and information prompting a change of the irradiation conditions.

(11)

The processing circuitry may cause the display device to display the first area and the second area in a distinguishable manner.

(12)

The processing circuitry may cause the display device to display the first area and the second area in the histogram in a visually distinguishable manner.

(13)

The processing circuitry may put a mark on the displayed histogram to indicate the first threshold.

(14)

The processing circuitry may cause the display device to display a numerical value(s) indicting a volume ratio(s) of the first area and/or the second area.

(15)

A radiotherapy planning method comprising:
setting irradiation conditions for a medical image relating to a patient;
acquiring a histogram of a radiation dose rate in a predetermined area in the patient based on the irradiation conditions;
evaluating the irradiation conditions based on the histogram; and
outputting information based on an evaluation result of the irradiation conditions.

(16)

A radiotherapy support apparatus comprising processing circuitry, the processing circuitry configured to:
calculate a positional deviation between a current position of a patient laid on a bed and a reference position;
determine whether or not the positional deviation is acceptable based on a comparison between a reference value and a volume ratio of an area relating to a predicted dose rate that falls below a threshold in healthy tissue of the patient corresponding to the current position; and
give an alert when it is determined that the positional deviation is not acceptable.

(17)

The reference value may be a volume ratio of an area relating to a predicted dose rate that falls below the threshold in the healthy tissue of the patient corresponding to the reference position.

(18)

The processing circuitry causes the display device to display a first histogram of a predicted dose rate relating to the current position and a second histogram of a predicted dose rate relating to the reference positon.

(19)

A radiotherapy planning apparatus comprising processing circuitry, the processing circuitry configured to:
set irradiation conditions;
calculate, based on irradiation conditions, a volume index value of an area relating to a predicted dose index value that falls below a first threshold; and
determine whether or not the irradiation conditions are acceptable based on the volume index value.

The irradiation conditions include at least an irradiation field and an irradiation dose index value that are set in a medical image.

(20)

The processing circuitry may determine that the irradiation conditions are not acceptable if the volume index value exceeds a second threshold and may determine that the irradiation conditions are acceptable if the volume index value falls below the second threshold.

(21)

The processing circuitry may generate a spatial distribution of the predicted dose index value relating to the irradiation field based on the irradiation conditions, generate a frequency distribution of the predicted dose index value relating to the healthy tissue based on the spatial distribution, and calculate the volume index value by applying the first threshold to the frequency distribution.

(22)

The processing circuitry may specify a first irradiation area irradiated with radiation of the penumbra and a second irradiation area irradiated with radiation unrelated to the penumbra. The processing circuitry may allocate a predicted dose index value reduced by a collimator to the first irradiation area and allocate a predict dose index value not reduced by the collimator to the second irradiation area, thereby generating the spatial distribution.

(23)

The radiotherapy planning apparatus may further comprise a display device configured to display the volume index value in numerical values or in a graph format.

(24)

The radiotherapy planning apparatus may further comprise a display device configured to display the volume index value relating to the first irradiation area and that relating to the second irradiation area in numerical values or in a graph format.

(25)

The processing circuitry may change the irradiation conditions in accordance with a user's instructions or a predetermined algorithm if it is determined that the irradiation conditions have been determined to not be acceptable. The processing circuitry may calculate a changed volume index value based on the changed irradiation conditions. The processing circuitry may determine whether or not the changed irradiation conditions are acceptable based on the changed volume index value.

(26)

The irradiation conditions may further include a direction of irradiation.

(27)

The first threshold may have a value with which a therapy effect from a high-dose ultrashort-time irradiation on the healthy tissue can be obtained.

(28)

If the irradiation field includes a plurality of healthy tissue portions, the processing circuitry may calculate the volume index value for each of the plurality of healthy tissue portions.

(29)

The predicted dose index value may be a predicted dose value and/or a predicted dose rate value. The volume index value may be a volume or a volume ratio.

(30)

A radiotherapy support apparatus comprising processing circuitry, the processing circuitry configured to:
calculate a positional deviation between a current position of a patient laid on a bed and a reference position;
determine whether or not the positional deviation is acceptable based on a comparison between a reference volume index value and a volume index value of an area relating to a predicted dose index value that falls below a threshold in healthy tissue of the patient corresponding to the current position; and
give an alert when it is determined that the positional deviation is not acceptable.

(31)

The reference volume index value may be a volume index value of an area relating to a predicted dose index value that falls below the threshold in the healthy tissue of the patient corresponding to the reference position.

(32)

The radiotherapy support apparatus may further comprise a first frequency distribution of the predicted dose index value relating to the current position and a second frequency distribution of the predicted dose index value of the reference position.

The invention claimed is:

1. A radiotherapy planning apparatus comprising processing circuitry, the processing circuitry configured to:
set irradiation conditions for a medical image relating to a patient;
acquire a histogram of a radiation dose rate in a predetermined area in the patient based on the irradiation conditions;
evaluate the irradiation conditions based on the histogram; and
output information based on an evaluation result of the irradiation conditions.

2. The radiotherapy planning apparatus according to claim 1, wherein
the processing circuitry determines suitability of the irradiation conditions based on the historgram.

3. The radiotherapy planning apparatus according to claim 2, wherein
the processing circuitry determines the suitability of the irradiation conditions based on a comparison between a first threshold and a volume ratio in the histogram of a first area or a second area to the irradiation area, the first area does not respond to a FLASH irradiation effect, the second area responds to a FLASH irradiation effect.

4. The radiotherapy planning apparatus according to claim 3, wherein
the processing circuitry specifies the first area and the second area in a medical image relating to the determined area or in the histogram.

5. The radiotherapy planning apparatus according to claim 4, wherein
the processing circuitry specifies a penumbra area in the predetermined area as the first area and specifies an area other than the penumbra area in the predetermined area as the second area.

6. The radiotherapy planning apparatus according to claim 4, wherein
the processing circuitry specifies the first area and the second area based on at least one of an irradiation depth of the radiation in the irradiation area, radiation absorption characteristics of tissue in the irradiation area, and a penumbra in the irradiation area.

7. The radiotherapy planning apparatus according to claim 4, wherein
the processing circuitry specifies the first area and the second area based on the histogram and a second threshold relating to the dose rate.

8. The radiotherapy planning apparatus according to claim 2, wherein
the processing circuitry determines the suitability of the irradiation conditions based on a comparison between a predicted dose and a tolerable dose of a tissue, the predicted dose being dose to the tissue in the first area that do not respond to FLASH irradiation effect.

9. The radiotherapy planning apparatus according to claim 2, wherein
the processing circuitry causes a display device to display information based on the suitability of the irradiation conditions.

10. The radiotherapy planning apparatus according to claim 9, wherein
if it is determined that the irradiation conditions are not suitable, the processing circuitry displays information prompting a change of the irradiation conditions as information based on the suitability of the irradiation conditions.

11. The radiotherapy planning apparatus according to claim 3, wherein
the processing circuitry causes the display device to display the first area and the second area in a distinguishable manner.

12. The radiotherapy planning apparatus according to claim 3, wherein
the processing circuitry causes the display device to display the histogram showing the first area and the second area in a visually distinguishable manner.

13. The radiotherapy planning apparatus according to claim 12, wherein
the processing circuitry puts a mark on the displayed histogram to indicate the first threshold.

14. The radiotherapy planning apparatus according to claim 3, wherein
the processing circuitry causes a display device to display a numeric value or numeric values indicating a volume ratio or volume ratios of the first area and/or the second area.

15. A radiotherapy planning method, the method comprising:
- setting irradiation conditions for a medical image relating to a patient;
- acquiring a histogram of a radiation dose rate in a predetermined area in the patient based on the irradiation conditions;
- evaluating the irradiation conditions based on the histogram; and
- outputting information based on an evaluation result of the irradiation conditions.

* * * * *